(12) United States Patent
Ophardt et al.

(10) Patent No.: US 12,103,847 B2
(45) Date of Patent: Oct. 1, 2024

(54) OZONE GENERATOR WITH SENSOR

(71) Applicant: OP-Hygiene IP GmbH, Niederbipp (CH)

(72) Inventors: Heiner Ophardt, Arisdorf (CH); Andrew Jones, St. Anns (CA)

(73) Assignee: OP-Hygiene IP GmbH, Niederbipp (CH)

( * ) Notice: Subject to any disclaimer, the term of this patent is extended or adjusted under 35 U.S.C. 154(b) by 221 days.

(21) Appl. No.: 16/743,259

(22) Filed: Jan. 15, 2020

(65) Prior Publication Data

US 2020/0223693 A1 Jul. 16, 2020

Related U.S. Application Data

(60) Provisional application No. 62/793,041, filed on Jan. 16, 2019.

(51) Int. Cl.
*C01B 13/11* (2006.01)
*A47K 5/12* (2006.01)
*A47K 5/14* (2006.01)
*A61L 2/18* (2006.01)
*A61L 2/24* (2006.01)

(52) U.S. Cl.
CPC ............ *C01B 13/11* (2013.01); *A47K 5/1217* (2013.01); *A47K 5/14* (2013.01); *A61L 2/183* (2013.01); *A61L 2/24* (2013.01); *A61L 2202/11* (2013.01); *C01B 2201/62* (2013.01); *C01B 2201/82* (2013.01); *C01B 2201/90* (2013.01)

(58) Field of Classification Search
CPC . C01B 13/11; C01B 2201/62; C01B 2201/82; C01B 2201/90; A61L 2/183; A61L 2/24; A61L 2202/11; A47K 5/1217; A47K 5/14
See application file for complete search history.

(56) References Cited

U.S. PATENT DOCUMENTS 5,052,382 A * 10/1991 Wainwright ............ A61M 1/32
128/202.25
5,540,898 A * 7/1996 Davidson .............. C01B 13/115
422/186.15

(Continued)

FOREIGN PATENT DOCUMENTS

CA 2225483 11/1996
CN 102671559 A * 9/2012

(Continued)

OTHER PUBLICATIONS

English Translation of CN-102671559-A (Year: 2012).*

(Continued)

*Primary Examiner* — Louis J Rufo

(74) *Attorney, Agent, or Firm* — Thorpe North & Western, LLP

(57) ABSTRACT

A method for monitoring ozone generation in an oxygen containing gas within a chamber in an ozone generator in which ozone is generated comprising: sensing with a sensor a parameter within the chamber with time; wherein the parameter is selected from the group consisting of sound and electromagnetic radiation and estimating an amount of ozone generated with time as a function of the parameter sensed by the sensor.

20 Claims, 13 Drawing Sheets

(56) References Cited

U.S. PATENT DOCUMENTS

| | | | |
|---|---|---|---|
| 5,644,070 A * | 7/1997 | Gibboney | A61L 2/202 |
| | | | 422/186.08 |
| 6,139,809 A | 10/2000 | Rodden | |
| 6,409,050 B1 | 6/2002 | Ophardt et al. | |
| 8,150,278 B2 | 4/2012 | Satoh et al. | |
| 8,362,921 B2 | 1/2013 | Pan | |
| 8,648,724 B2 | 2/2014 | Forsberg | |
| 8,733,596 B2 * | 5/2014 | Ophardt | B05B 11/308 |
| | | | 222/190 |
| 9,025,783 B2 | 5/2015 | Mahowald | |
| 9,995,621 B2 | 6/2018 | Rose et al. | |
| 10,192,539 B2 | 1/2019 | Starobin | |
| 10,203,711 B2 | 2/2019 | Wegelin | |
| 10,935,522 B2 | 3/2021 | Niemann et al. | |
| 2005/0199484 A1 | 9/2005 | Olstowski | |
| 2006/0237483 A1 | 10/2006 | Ophardt | |
| 2009/0045221 A1 | 2/2009 | Ophardt et al. | |
| 2009/0145296 A1 | 6/2009 | Ophardt et al. | |
| 2012/0187840 A1 * | 7/2012 | Hensley | H05H 1/0093 |
| | | | 315/111.21 |
| 2017/0203101 A1 | 7/2017 | Van den Heuvel | |
| 2018/0336274 A1 | 11/2018 | Choudhury et al. | |
| 2019/0239796 A1 | 8/2019 | Avrahamson | |
| 2019/0311587 A1 | 10/2019 | Ophardt et al. | |

FOREIGN PATENT DOCUMENTS

| | | | | |
|---|---|---|---|---|
| EP | 0339924 | | 11/1989 | |
| EP | 1257888 A2 * | | 11/2002 | A61L 9/22 |
| EP | 3686622 | | 7/2020 | |
| JP | H02293304 | | 12/1990 | |
| JP | H04270102 | | 9/1992 | |
| JP | H05306105 | | 11/1993 | |
| JP | 2001212221 A * | | 8/2001 | |
| WO | 2008034446 | | 3/2008 | |

OTHER PUBLICATIONS https://web.archive.org/web/20130110004251/https://www.lenntech.de:80/bibliothek/ozonherstellung-ozone-generation.htm. Lenntech Bv. Ozone Generation. Jan. 10, 2013.

https:/web.archive.org/web/20160913143326/http://www.electricaleasy.com/2016/07/corona-discharge.html electriceasy.com; Kiran Daware; Corona Discharge—Its Effects and Methods of Reducing It. Jul. 2016.

https://electric.atco.com/content/dam/web/projects/projects-overview/electricity/noise-final-may-21-2014.pdf; ATCO Electric; Edmonton, Alberta, Canada; Web Page—Will you hear the transmission line? www.atcoelectric.com. May 21, 2014.

https://web.archive.org/web/20181202181944/https://en.wikipedia.org/wiki/Corona discharge; Wikipedia—Corona Discharge; Dec. 2, 2018.

* cited by examiner

OZONE GENERATOR WITH SENSOR

SCOPE OF THE INVENTION

This invention relates to a method and apparatus of generating ozone and, more particularly, to a method of dispensing and dispensers for dispensing hand cleaners fluids containing a foam of ozonated air and a liquid.

BACKGROUND OF THE INVENTION

Many fluids are known as useful for cleaning and disinfecting.

Ozone ($O_3$) is a strong oxidizing agent having an oxygenation potential more than 1.5 times that of chlorine and approximately 1.2 times that of hydrogen peroxide. Ozone is normally produced by passing an oxygen-containing gas through ultraviolet light or a corona discharge. Ozone has been shown to be a relatively reactive oxidant capable of destroying pathogenic microorganisms. Ozone naturally decomposes into oxygen within relatively short periods of time.

Hand cleaner dispensers are known, such as disclosed in U.S. Pat. No. 8,733,596 issued 2014 May 27 to Ophardt et al, which generate and dispense ozone in a foam of gas and liquid onto a person's hands for cleaning, sanitizing and disinfecting the hands.

The present applicants have recognized a disadvantage of such ozone foam dispensers is the absence of a practical system providing an ability towards establishing the ozone generator has generated and dispensed an accurate amount of ozone as during a dispensing cycle in which an allotment of ozone foam is discharged. Such disadvantages are particularly acute with ozone foam dispensers in that the dispensers are often operated intermittently with periods of use following periods of non-use and in which ozone generators are often generating ozone under start up and fluctuating conditions rather than steady state. Such disadvantages are also particularly acute with ozone gas generators and foam dispensers that are powered by batteries without access to an external power supply such as an A/C building power supply.

The present applicants have recognized that known ozone sensors for sensing ozone gas suffer disadvantages and have many downfalls including, but not limited to large size, cost, and power consumption, speed of sensing and limitations of concentration ranges that can be sensed. For example, known ozone sensors often require at least 2 seconds for reading and many ozone sensors do not cover concentration ranges in excess of 10 ppm while sensing of concentrations up to 100 ppm may be required.

The present applicants have recognized that known ozone sensors have the disadvantages that they are not relatively low cost; that they cannot operate on low electrical power, voltage and/or current draws and that they cannot respond quickly enough to provide desired amounts of ozone during operation of a typical soap dispense event which lasts about 1-2 seconds in its entirety. The present applicants have recognized that known ozone sensors have the disadvantage that they cannot respond quickly enough as, for example, in ½ second as to be able to sense and establish that adequate ozone has been generated before discharge of ozonated foam from a dispenser of hand cleaner without providing a delay in discharge that would likely annoy a user.

Disadvantages also arise as to how, where and when the level of ozone is to be sensed. If sensing is after the foam is produced, such sensing for the amount of ozone in the foam itself is appreciated by the applicants as being problematic as the ozone has only a short half-life when ensconced in foam and an act of "bursting" the bubbles would likely need to be completed prior to sensing.

Presently known devices do not provide for adequate methods or apparatus for monitoring and controlling generation and dispensing of small amounts of ozone as can be useful, for example, in dispensers of hand cleaners.

SUMMARY OF THE INVENTION

To at least partially overcome some of these disadvantages of previously known devices, the present invention provides methods and apparatus for monitoring and/or controlling generation and dispensing of ozone, preferably, in an apparatus for dispensing hand cleaners including disinfectants and sanitizers.

To at least partially overcome some of these disadvantages of previously known devices, the present invention provides a method for monitoring ozone generation by an ozone generator in which ozone is generated by converting oxygen with an oxygen containing gas comprising: sensing with a sensor, a parameter preferably selected from one or more of the group consisting of sound and electromagnetic radiation, and estimating an amount of ozone generated as a function of the parameter sensed by the sensor. Preferably, the generating of ozone is carried out in a chamber and the method includes one or more of drawing atmospheric air into the chamber, generating ozone within the chamber, and discharging the ozonated air from the chamber. The sensor may be within the chamber or outside the chamber. Preferably, the sensors sense the parameter with time and estimating an amount of ozone generated with time as a function of the parameter sensed by the sensor. Preferably, based on the estimating of the amount of ozone generated with time, the step of generating ozone within the chamber is controlled to generate a desired amount of ozone. Optionally, the method includes mixing the ozonated air with a foamable fluid to form an ozonated fluid air mixture.

To at least partially overcome other disadvantages of the previously known devices, the present invention provides an ozone generator including a sensor to assist in assessing the ozone generated by the ozone generator with time by sensing a parameter that bears a relationship with the amount of ozone produced. Preferably, a processor is provided to receive an output from the sensor representing the parameter sensed with time and to estimate the amount of ozone generated with time as a function of the parameter sensed by the sensor. The estimate of the ozone generated may then be used to control the operation of the ozone generator and other apparatus with which the ozone is associated including a dispenser of hand cleaner that dispenses a foam of ozonated air and a liquid onto a person's hand. The parameter is preferably selected from one or more of the group consisting of sound and electromagnetic radiation.

The nature of the ozone generator is not limited. Ozone generators which can be used include generators which discharge electromagnetic radiation through an oxygen containing gas including corona discharge ozone generators and ultraviolet light ozone generators.

As used in this application, corona discharge ozone generators include open spark type corona discharge ozone generators in which electricity is passed through air between two electrodes at different electrical potentials to form ozone in the air and dielectric ozone generators such as single dielectric ozone generators and dual dielectric ozone generators including cold plasma generators. Examples of dielectric ozone generators include those taught by U.S. Pat. No. 6,139,809 to Rodden, issued Oct. 31, 2000 and US Patent Publication 2005/0199484 to Olstowski, published Sep. 15, 2005. Dielectric ozone generators are preferred as they have greater generation density and are more energy efficient than open spark type corona discharge ozone generators.

Ultra violet light ozone generators emit UV light to generate ozone from oxygen as in air. The UV light emitters are preferably LED based emitters.

Preferably, when the ozone generator comprises a corona discharge mechanism to produce ozone, the sensor is for sensing a parameter selected from the group consisting of: a) electromagnetic radiation produced by corona discharge mechanism while operative to convert oxygen into ozone produced, and b) sound produced by corona discharge mechanism while operative to convert oxygen into ozone.

When the ozone generator comprises an ultraviolet radiation emitting mechanism to produce ozone, the sensor preferably senses electromagnetic radiation discharged by the ultraviolet radiation emitting mechanism.

The sensor may sense one or both of electromagnetic radiation having a frequency which is the same as a frequency of the discharged electromagnetic radiation by the ultraviolet radiation emitting mechanism and electromagnetic radiation having a frequency which is different than the frequency of the discharged electromagnetic radiation by the ultraviolet radiation emitting mechanism.

The sensor can be within a chamber within which the ozone is produced or outside of the chamber as by sensing through a wall of the chamber.

The electromagnetic radiation sensed by the sensor is preferably selected from one or more of: visible light, ultraviolet light and infrared light.

The sound sensed by the sensor may be any frequency of sound including ultrasonic sound and infrasonic sound.

Another object of the present invention is to provide a method and apparatus for generating ozonated air in small amounts as suitable for use in dispensing from, for example, a wall mounted hand cleaning fluid dispenser that is preferably battery powered and preferably, with the discharge as an ozonated foam of the ozonated air and a liquid.

A dispensing assembly to produce ozone may be operated by electrical energy as from an electrical power source, such as by being wired to an A/C utility power supply system or, more preferably, batteries, or optionally may be manually operated and in which electrical energy to create the ozone may be supplied by a manually operated electrical generator that is operated to both generate ozone and dispense a hand cleaner containing the ozone.

In one aspect, the present invention provides a dispenser dispensing ozone containing foam comprising:
  an ozone generator comprising an ozone generating chamber,
  the ozone generating chamber having an air inlet in communication with a source of air and an outlet,
  an ozone generating mechanism within the ozone generating chamber to generate ozone from air in the ozone generating chamber by conversion within the ozone generating chamber of oxygen in the air within the ozone generating chamber into ozone to form ozonated air, and
  a sensor to assess a parameter arising by the operation of the ozone generating mechanism in generating ozone that bears a relationship with the amount of ozone produced.

Preferably, the dispenser includes an air pump for passing air through the ozone generating chamber to discharge an ozonated air stream. Preferably, the dispenser also includes a foam generator and a liquid pump operative to draw liquid from a reservoir and discharge a liquid stream to the foam generator for simultaneous passage of the ozonated air stream which has been discharged from the ozone generating chamber and the liquid stream which has been discharged from the liquid pump through the foam generator to generate an ozonated foam for discharge out a discharge outlet as, for example, onto a person's hand.

In accordance with the present invention, a sensor is provided and used for sensing a parameter arising in the operation of an ozone generating mechanism that bears a relationship with the amount of ozone produced. The ozone generating mechanism preferably is selected from the group consisting of one or more of a corona discharge mechanism and an ultraviolet emitting mechanism. The ozone may be generated in an ozone generator as in an ozone generating chamber within which ozone is generated, however, the invention does not require the ozone to be generated within a chamber and the method of monitoring ozone is applicable to ozone being generated in atmospheric air as in, for example, a corona discharge mechanism open to the atmosphere.

In the context of an ozone generator including a corona discharge mechanism, the corona discharges a spark which is passed through an air gap between electrodes of different electrical potentials. Oxygen molecules in the air gap are exposed to electrical discharge to form ozone. This spark produces electromagnetic radiation typically including, amongst other things, visible light. The applicants have observed that the visible light varies in operation of the corona discharge mechanism. During the time from initial start-up until a relatively steady state of operation of the corona discharge mechanism, the location from which the visible light is generated on the electrodes, the intensity of the visible light generated, the wavelengths of the visible light, and the number of discharge sparks that generate visible light varies, typically increasing. When the corona discharge mechanism is operating in a relatively steady state, then the visible light is steadier, that is, more constant, as to locations, the number of locations, wavelengths, frequency and duration. The applicants have appreciated that the visible light emitted by the corona discharge mechanism represents an extent to which there is corona discharge and thus bears a relationship to the amount of ozone created with time.

In a similar manner that the individual corona discharges create electromagnetic radiation in the visible light spectrum, the corona discharge also produces electromagnetic radiation in a wide range of wavelengths. These wavelengths include low range ultraviolet wavelengths in the range of 185 nM which would be expected in the breakdown of oxygen to form ozone.

In measuring the electromagnetic radiation within the ozone generator chamber, a broad spectrum of electromagnetic radiation of different wavelengths may be sensed or merely some preferred wavelengths may be sensed. The wavelengths are assessed as to their intensity and their frequency and, as well, may be sensed as to the location of the emission. The applicants have found that the electromagnetic radiation sensed having regard to factors including intensity, frequency, wavelength and location have been found to bear relationships to the amount of ozone that is produced in the ozone generator with time.

In addition to electromagnetic radiation, the applicants have found that in an ozone generator with a corona discharge mechanism, sound is often produced. The applicants have appreciated that during operation of the corona discharge mechanism, sound in the audible range is produced and the wavelength, frequency and intensity of the sound bears a relationship to the amount of ozone being produced by time. The sensor can measure sound at various different wavelengths or ranges of wavelengths and the sound which is measured with time at different wavelengths, at different intensity and frequency and, as well, at different locations bears relationships with the amount of ozone being produced.

In an ozone generator including an ultraviolet emitting mechanism, there is an input into the ozone generating chamber of UV radiation. The UV light emitted into the ozone generating chamber can be measured by a sensor as to wavelength, intensity and frequency and bears a relationship to the amount of ozone produced within the ozone generating chamber.

In accordance with the present invention, specific configurations of ozone generators are operated to produce ozone numerous times and under varying conditions including varying conditions of temperature, pressure and humidity. During such conditions, measurements are made with the sensors as to various parameters and the information or data developed from the sensors is used to provide functional relationships between the parameters sensed and the ozone generated with time, which such relationships can be used to make an assessment or estimate as to ozone produced in an ozone generator having the same or similar configurations.

In a 1st aspect, the present invention provides a method for monitoring ozone generation by an ozone generator in which ozone is generated by converting oxygen with an oxygen containing gas comprising:
  sensing with a sensor a parameter created with time,
  wherein the parameter is selected from one or more of the group consisting of sound and electromagnetic radiation, and
  estimating an amount of ozone generated with time as a function of the parameter sensed by the sensor.

In a $2^{nd}$ aspect, the present invention provides a method as in the $1^{st}$ aspect, including forming ozone from the oxygen containing gas with the ozone generator by discharge of electromagnetic radiation through the oxygen containing gas.

In a $3^{rd}$ aspect, the present invention provides a method as in the $2^{nd}$ aspect wherein the discharge of electromagnetic radiation through the oxygen containing gas is by corona discharge through the oxygen containing gas.

In a $4^{th}$ aspect, the present invention provides a method as in the $1^{st}$ aspect wherein the generation of the ozone is carried out in a chamber.

In a $5^{th}$ aspect, the present invention provides a method as in the $2^{nd}$ or $3^{rd}$ aspect wherein the generation of the ozone is carried out in a chamber.

In a $6^{th}$ aspect, the present invention provides a method as in the $4^{th}$ or $5^{th}$ aspect including at least one of delivering atmospheric air to the chamber to be the oxygen containing gas.

In a $7^{th}$ aspect, the present invention provides a method as in the $4^{th}$ or $5^{th}$ aspect including discharging oxygen containing gas including ozone from the chamber.

In an $8^{th}$ aspect, the present invention provides a method as in any one of the $4^{th}$ to $7^{th}$ aspects wherein the sensor is within the chamber.

In an $9^{th}$ aspect, the present invention provides a method as in any one of the $4^{th}$ to $7^{th}$ aspects wherein the sensor is outside to the chamber.

In a $10^{th}$ aspect, the present invention provides a method as in any one of the $1^{st}$ to $9^{th}$ aspects wherein the parameter comprising electromagnetic radiation, the sensor comprises an electromagnetic radiation sensor, and the method includes:
  sensing with the electromagnetic radiation sensor electromagnetic radiation created with time, and
  estimating an amount of ozone generated with time as a function of the electromagnetic radiation sensed by the sensor.

In an $11^{th}$ aspect, the present invention provides a method as in the $10^{th}$ aspect wherein the electromagnetic radiation sensor senses electromagnetic radiation selected from the group consisting of one or more of: electromagnetic radiation having a frequency which is the same as a frequency of the discharged electromagnetic radiation and electromagnetic radiation having a frequency which is different than the frequency of the discharged electromagnetic radiation.

In a $12^{th}$ aspect, the present invention provides a method as in any one of the $1^{st}$ to $11^{th}$ aspects wherein the electromagnetic radiation sensed by the sensor is selected from one or more of: visible light, ultraviolet light and infrared light.

In a $13^{th}$ aspect, the present invention provides a method as in any one of the $1^{st}$ to $12^{th}$ aspects wherein the parameter comprises sound and sensor comprises a sound sensor, the method including:
  sensing sound with a sound sensor sound created with time, and
  estimating an amount of ozone generated with time as a function of the sound sensed by the sensor.

In a $14^{th}$ aspect, the present invention provides a method as in any one of the $1^{st}$ to $13^{th}$ aspects including sensing with time at least one gas condition of the oxygen containing gas selected from the group of: temperature, humidity and pressure, and estimating the amount of ozone generated with time as a function of the parameter sensed by the sensor and at least one gas condition.

In a $15^{th}$ aspect, the present invention provides a method as in any one of the $1^{st}$ to $14^{th}$ aspects including forming ozone from the oxygen containing gas by discharge of ultraviolet light through the oxygen containing gas within the chamber.

In a $16^{th}$ aspect, the present invention provides an ozone generator comprising:
  a corona discharge mechanism operative to convert oxygen into ozone,
  a sensor for sensing with time a parameter selected from the group consisting of:
  i) sound produced by a corona discharge mechanism while operative to convert oxygen into ozone, and
  ii) electromagnetic radiation produced by a corona discharge mechanism while operative to convert oxygen into ozone produced,
  a processor to receive an output from the sensor representing the parameter sensed with time and to estimate the amount of ozone generated with time as a function of the parameter sensed by the sensor.

In a $17^{th}$ aspect, the present invention provides an ozone generator as in the $16^{th}$ aspect including:
  a power supply providing power to the corona discharge mechanism to render the corona discharge mechanism operative to convert oxygen into ozone, the processor controlling wherein the amount of ozone generated with time is a function of the nature of the power providing to the corona discharge mechanism by the power supply, the processor controlling the amount of ozone generated with time by control of the nature of the power providing to the corona discharge mechanism by the power supply, and as a function of the estimate the amount of ozone generated with time.

In an 18th aspect, the present invention provides an ozone generator as in the 16th or 17th aspect including:

at least one gas condition sensor selected from the group of: a temperature sensor, a humidity sensor and a pressure sensor of the oxygen containing gas, the processor to receive an output from the at least one gas condition sensor of temperature, humidity and pressure sensed with time and to estimate the amount of ozone generated with time as a function of the parameter sensed by the sensor and the temperature, humidity and pressure sensed by the at least one gas condition sensor with time.

In a 19th aspect, the present invention provides an ozone generator as in the 16th to 18th aspects wherein:

the corona discharge mechanism including a chamber within which an oxygen containing gas is provided to convert oxygen in the oxygen containing gas into ozone, a pumping system operative to supply oxygen containing gas to the chamber and to discharge the oxygen containing gas from the chamber.

In a 20th aspect, the present invention provides an ozone generator as in the 19th aspect wherein the processor controls the operation of the pumping system.

In a 21st aspect, the present invention provides an ozone generator as in the 20th aspect wherein the processor controls the operation of the pumping system as a function of the estimate the amount of ozone generated with time.

In a 22nd aspect, the present invention provides a hand cleaner dispenser dispensing a foamed mixture of an ozonated air and a liquid, the dispenser including an ozone generator as in the 16th to 21st aspects.

In a 23rd aspect, the present invention provides a dispenser dispensing ozone containing foam comprising:

an ozone generator comprising an ozone generating chamber, the ozone generating chamber having an air inlet in communication with a source of air and an outlet, an ozone generating mechanism within the ozone generating chamber to generate ozone from air in the ozone generating chamber by conversion within the ozone generating chamber of oxygen in the air within the ozone generating chamber into ozone to form ozonated air, and a sensor to assess a parameter arising by the operation of the ozone generating mechanism in generating ozone that bears a relationship with the amount of ozone generated.

In a 24th aspect, the present invention provides a dispenser as in the 23rd aspect wherein the dispenser includes an air pump for passing air through the ozone generating chamber to discharge an ozonated air stream.

In a 25th aspect, the present invention provides a dispenser as in the 24th aspect wherein the dispenser includes a foam generator and a liquid pump operative to draw liquid from a reservoir and discharge a liquid stream to the foam generator for simultaneous passage of the ozonated air stream which has been discharged from the ozone generating chamber and the liquid stream which has been discharged from the liquid pump through the foam generator to generate the ozonated foam for discharge out a discharge outlet.

In a 26th aspect, the present invention provides a method of operating a hand cleaner dispenser comprising:

generating ozone in an ozone generator in a chamber in which ozone is generated by converting oxygen in an oxygen containing gas to ozone to produce ozonated air containing ozone, passing the ozonated air and a liquid through a foam generator to generate a foamed mixture of the ozonated air and the liquid out a discharge outlet, sensing with a sensor a parameter selected from one or more of the group consisting of sound and electromagnetic radiation created by operation of the ozone generator, estimating an amount of ozone generated with time as a function of the parameter sensed by the sensor, controlling the operation of the ozone generator as a function of the estimate the amount of ozone generated.

In a 27th aspect, the present invention provides a method as in the 26th aspect including controlling the operation of the ozone generator as a function of the estimate the amount of ozone generated and the ozonated air passed through the foam generator.

In a 28th aspect, the present invention provides a method as in the 26th or 27th aspect including sensing at least one gas condition of the oxygen containing gas selected from the group of: temperature, humidity and pressure, and estimating the amount of ozone generated with time as a function of the parameter sensed by the sensor and the at least one gas condition.

BRIEF DESCRIPTION OF THE DRAWINGS

Further aspects and advantages of the present invention will be apparent from the following description taken together with the accompanying drawings in which.

DETAILED DESCRIPTION OF THE DRAWINGS

Figure 1:
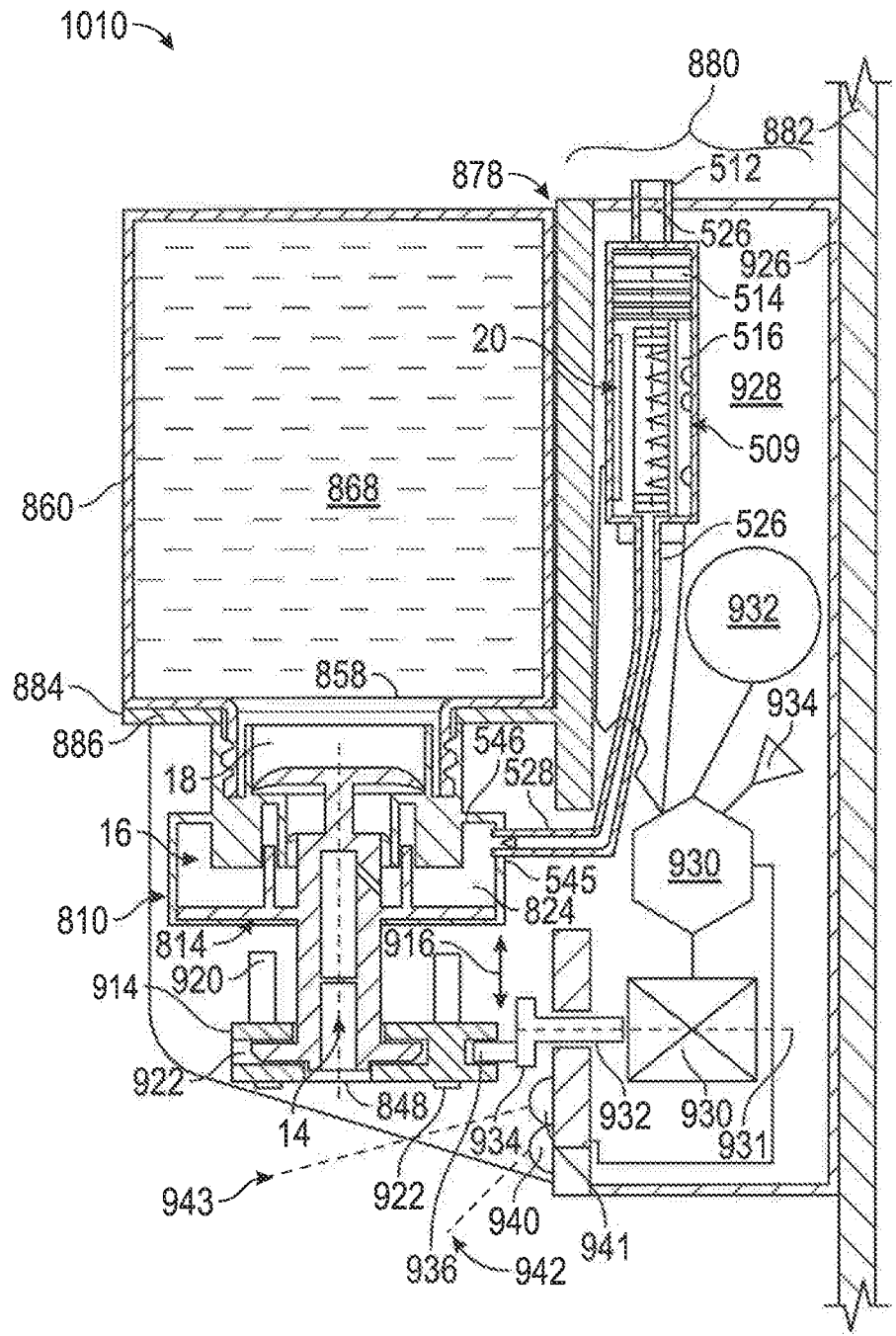
FIG. 1 is a schematic cross-sectional view of a first embodiment of a dispenser for dispensing ozone foam using a corona discharge unit in combination with a piston pump and showing the piston pump in a withdrawn position.

Reference is made to FIGS. 1 to 5, 9 and 10 which show a first embodiment of a dispenser 1010 in accordance with the present invention. The dispenser 1010 includes an ozone generator 509 in which ozone is created from atmospheric air, a foam generator 14, an air pump 16 to pass air through the ozone generator 509 and deliver ozonized air to the foam generator 14, and a liquid pump 18 to deliver a liquid from a reservoir 860 to the foam generator 14. The air pump 16 and liquid pump 18 are provided by a pump assembly 810.

Figure 3:
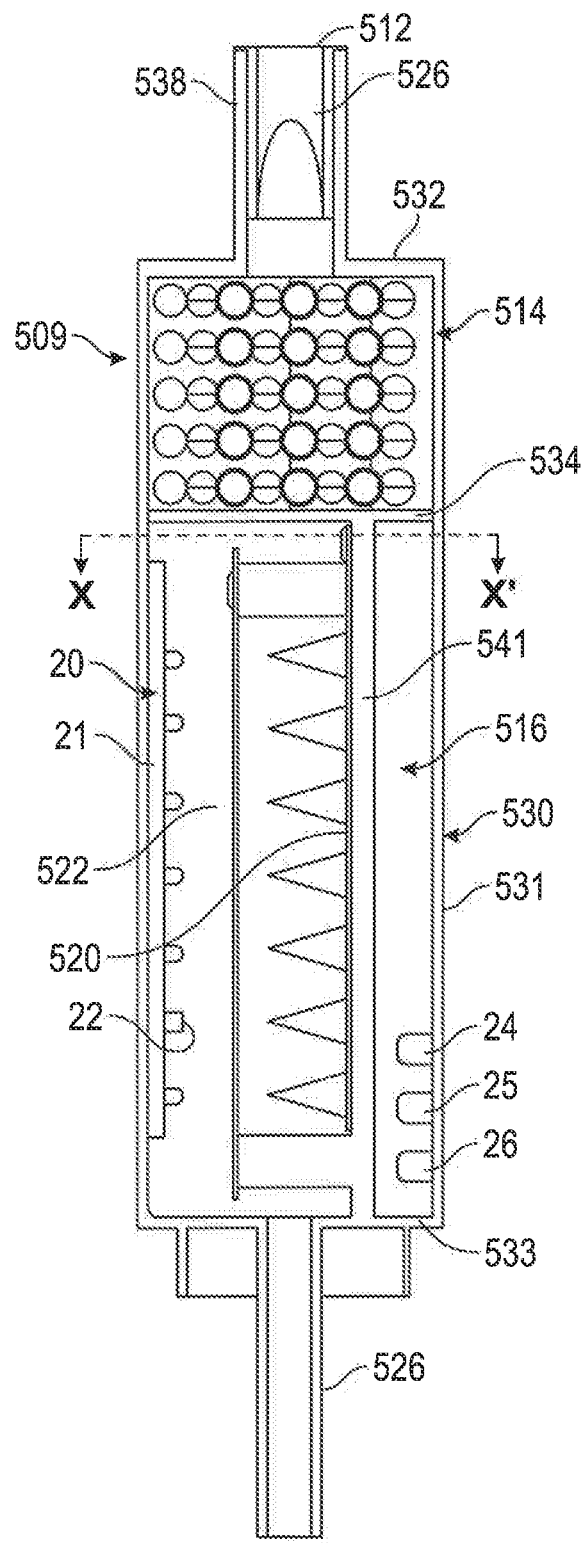
FIG. 3 is a side view of an ozone generator with a corona discharge mechanism as shown in FIG. 1.
Figure 4:
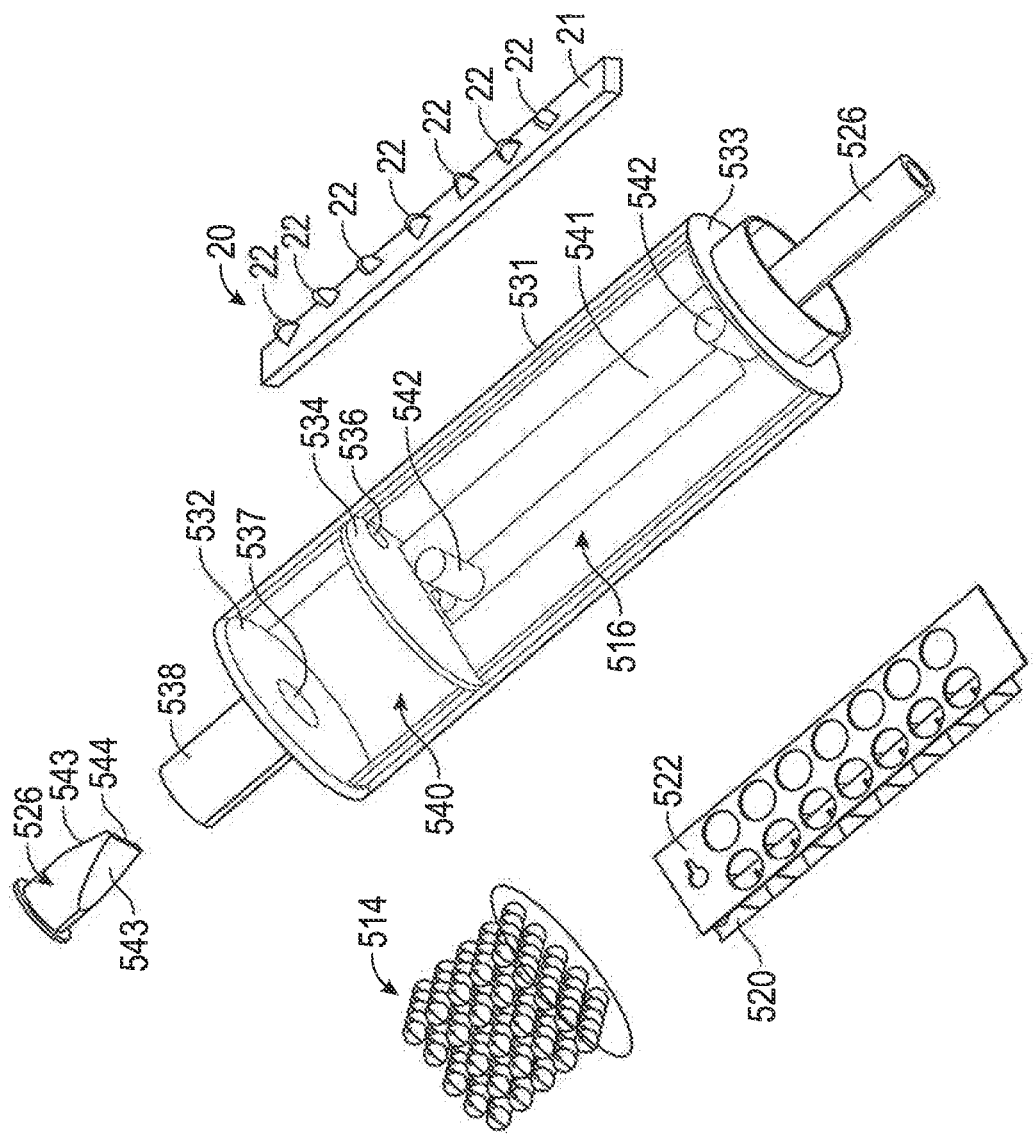
FIG. 4 is an exploded view of the ozone generator shown in FIG. 3.
Figure 5:
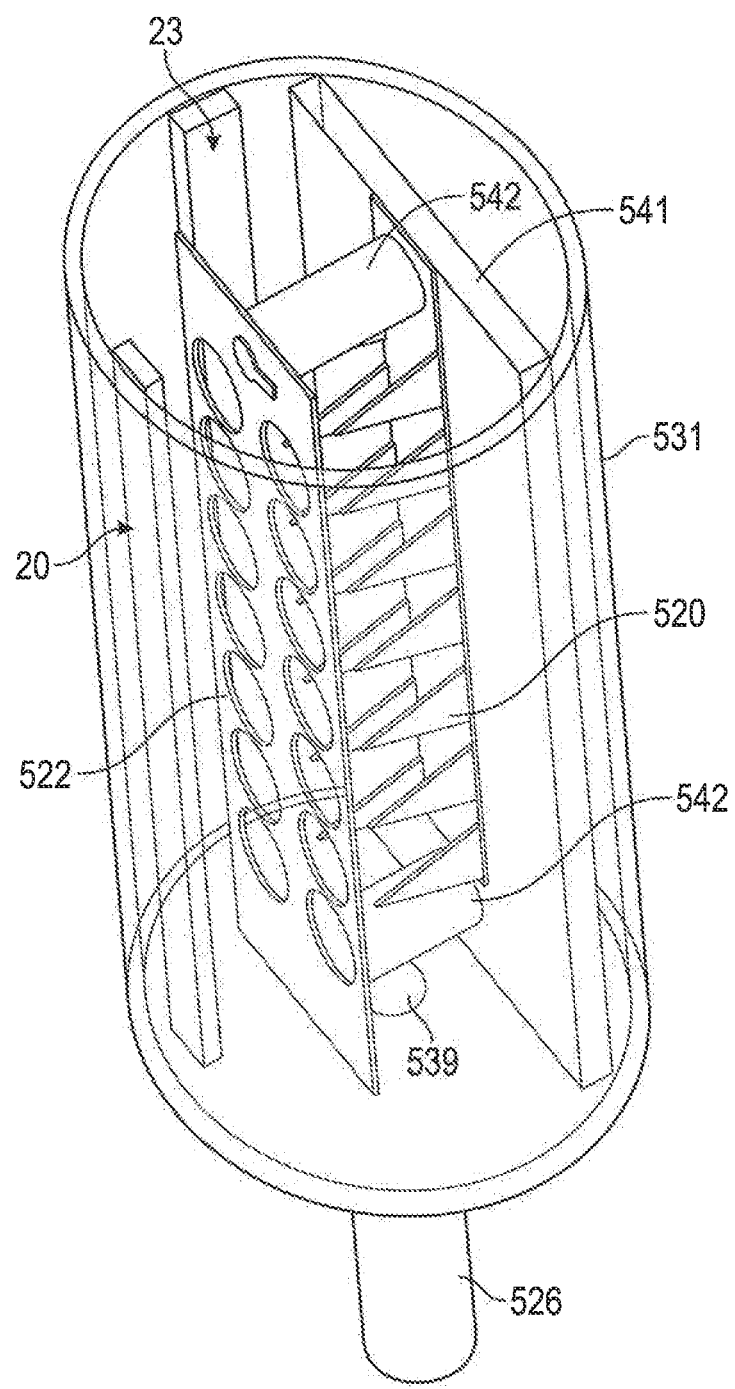
FIG. 5 is a side pictorial view of the ozone generator of FIG. 3 as seen below section line X-X' in FIG. 3.

Reference is made to FIGS. 3 to 5 showing additional details of the ozone generator 509. The ozone generator 509 includes a housing 530 which includes a generally cylindrical outer wall 531, an inner end wall 532 and an outer end wall 533. An intermediate dividing wall 534 is provided in between the inner end wall 532 and the outer end wall 533. An inlet opening 536 is provided axially through the dividing wall 534. The inner end wall 532 has an opening 537 therethrough which connects with an atmospheric air inlet tube 538. The outer end wall 533 has an outlet opening 539 therethrough which connects with the ozone delivery tube 526. A passageway for air flow is thus provided through the ozone generator 509 through the inlet tube 538, through the inner end wall 532 via the inlet opening 537, through the dividing wall 534 via the opening 536 and through the outer end wall 533 via the opening 539 to ozone delivery tube 526.

An air drying chamber 540 is formed within the housing 530 between the inner end wall 532 and the dividing wall 534 within which the drying air filter 514 is provided. The drying air filter 514 is shown as a matrix of media and which serves the purpose of removing moisture from air which passes through the drying chamber 540.

An ozone generating chamber 516 is defined between the dividing wall 534 and the outer end wall 533 within the housing. A flat electrically non-conductive support plate 541 extends axially between the dividing wall 534 and the outer end wall 533. A corona discharge mechanism 517 is provided within the ozone generating chamber 516 including a first electrode 520 and a second electrode 522. The first electrode 520 is mounted flush with the support plate 541. The second electrode 522 is mounted spaced from the first electrode 520 and electrically insulated thereof by reason of two insulating posts 542. While not shown in the drawings, each of the electrodes 520 and 522 is connected to an electrical source such that there is electrical discharge between the electrodes 520 and 522 through air in the ozone generating chamber 516 to form ozone from oxygen in the air.

The ozone generator 509 includes a sensor mechanism 20 for sensing with time at least one parameter within the ozone discharge chamber 516 chamber. The parameter is selected to be a relatively easily sensed parameter that bears a relationship with the amount of ozone produced. The applicants have appreciated that parameters that bear a relationship with the amount of ozone produced in the ozone generator 509 with a corona discharge mechanism include parameters selected from the group consisting of:
 a. electromagnetic radiation produced by corona discharge mechanism while operative to convert oxygen into ozone produced, and
 b. sound produced by the corona discharge mechanism while operative to convert oxygen into ozone.

The sensor mechanism 20 is best shown in FIGS. 3 to 5 as comprising an elongate strip 21 secured to an inside surface of the outer wall 531 of the housing 530 spaced from and in opposition to the second electrode 522. The strip 21 has an ability to sense one or more parameters along its length and is illustrated as having a plurality of individual sensors 22 spaced longitudinally along its length. Providing the sensor mechanism 20 as an elongate strip 21 with various sensors along its length can be of assistance in sensing the parameters within the ozone generating chamber 516 at various locations along the length of the ozone generating chamber 516 which can be of assistance in estimating the amount of ozone produced. As shown only in FIG. 5, the sensor mechanism 20 may include in addition to the sensor strip 21, a secondary sensor strip 23 disposed at a different circumferential location. Providing the sensor mechanism 20 so as to be able to sense parameters at different locations within the ozone generating chamber 516 can be advantageous to more precisely measure parameters arising when ozone is produced in the ozone generator chamber 516.

The ozone generator 509 may preferably include other sensors such as preferably a temperature sensor 24, a pressure sensor 25 and a humidity sensor 26 shown only on FIG. 3 to provide additional input as to the conditions arising within the ozone generating chamber 516 which can be used to assist in estimating the amount of ozone that may be produced and provide feedback as to a control mechanism 509 to control the operation of the dispenser.

The ozone generator 509 as well as the sensor mechanism 20, the temperature sensor 24, the pressure sensor 25 and the humidity sensor 26 are connected to and controlled by a control mechanism 930. The control mechanism 930 controls the generation of ozone by the ozone generator 509. The control mechanism 930 preferably also controls the sensor mechanism 20 to sense parameters in the ozone generator 509 and the operation of the temperature sensor 24, the pressure sensor 25 and the humidity sensor 26. The control mechanism 930 further controls the operation of the pump assembly 810.

The parameters sensed by the sensor mechanism 20 is feedback or output information which is provided to the control mechanism 509. The control mechanism 930 includes a processor to receive the output information from the sensor mechanism 20 representing the parameter sensed with time and to estimate the amount of ozone generated with time as a function of the parameters sensed by the sensor. In estimating the amount of ozone generated the processor preferably also to receive the output information from the temperature sensor 24, the pressure sensor 25 and the humidity sensor 26.

The control mechanism 930 may use the output information in many desired manners to control the operation of the dispenser 1010. For example, the control mechanism 930 may delay the discharge of ozonated foam until an adequate amount of ozone is produced. The delay may be created various ways including by delaying operation of the pump assembly 810, or slowing the speed of operation the pump assembly 810. If the control mechanism 930 may determine that inadequate ozone has been created or dispensed in one or more doses dispensed, the control mechanism 930 may signal a user to take another dose. The control mechanism 930 may adjust the operation of the ozone generator 509 including changing the power, voltage, amperage or frequency of electrical power supplied or the duration of operation, or the time of initiation or discontinuance of operation to increase or decrease the amount of ozone created.

The control mechanism 930 may control the sensor mechanism 20 to sense the parameters at all times while the ozone generator 509 is operative to generate ozone. However, toward reducing the electrical power to operate the dispenser, the control mechanism 930 may control the sensor mechanism 20 so as to not sense the parameters at all times while the ozone generator 509 is operative to generate ozone but rather only at selected times as, for example, periodically to sense the parameters. For example, when the ozone generator is considered to be operating in what might be considered a steady state condition and after ozone generation may have been estimated to be within certain parameters, then the control mechanism 930 may control the sensor mechanism 20 so as to not operate for a number of dispensing activations, or a period of time or based on some other factor.

In operation of the ozone generator 509, the air pump 16 causes atmospheric air to enter the air inlet 512 and to pass through the drying air filter 514 and into the ozone generating chamber 516 in which ozone is created and, hence, delivered via the ozone delivery tube 526 into the cylindrical outer chamber 824 of the pump assembly 810. A one-way inlet valve 526 is preferably provided to permit atmospheric air to enter into the ozone generator 509 but to prevent gases inside the generator from passing outwardly. FIG. 4 shows the one-way inlet valve 526 as comprising a duck-bill type plastic valve which can be formed by injection molding and includes, as seen in FIG. 4 at its lower end, a pair of opposed flat sides 543 which are biased together at a slit line opening 544. The bias of the two sides 543 together can be overcome by creating a relative vacuum within the ozone generator 509 by operation of the pump assembly 812.

A one-way outlet valve 528 is preferably provided in the ozone delivery tube 526 from the ozone generator to permit one-way flow of ozone from the ozone generator 509 into the pump assembly 810 but to prevent flow of fluid such as liquid, foam and/or gas from the pump assembly 810 back into the ozone generator 509. Preferably, the one-way outlet valve 528 may also comprise a similar duck-bill valve to that illustrated in FIG. 4 as the one-way inlet valve 526.

The dispenser 1010 includes the pump assembly 810 secured in the neck of a sealed, collapsible container or reservoir 860 containing liquid hand soap 868 to be dispensed. Dispenser 1010 has a housing generally indicated 878 to receive and support the pump assembly 810 and the reservoir 860. Housing 878 is shown with a back plate assembly 880 for mounting the housing, for example, to a building wall 882. A support plate 884 extends forwardly from the back plate assembly 880 to support and receive the reservoir 860 and pump assembly 810. The bottom support plate 884 has a forwardly opening 886 therethrough. The reservoir 860 sits supported on the support plate 884 with the neck 858 of the reservoir 860 extending through opening 886 and secured in the opening as by a friction fit, clamping and the like.

An actuator slide plate 914 is slidably mounted to the housing 878 for limited vertical movement in the direction indicated by the arrow 916. In a known manner, the housing 878 may have two side plates with one side plate 915 on each lateral side thereof which extends downwardly from the support plate 884. The actuator slide plate 914 may extend laterally between these side plates 918 of the dispenser and be engaged within vertical slide grooves 920 and 922 shown in each side plate 915 to guide the slide plate 914 in vertical sliding. The actuator slide plate 914 has a forwardly opening cavity 922 formed therein such that the piston 814 may be slid rearwardly into the cavity 922 so as to receive the engagement flange 862 within the cavity and couple the piston 814 to the slide plate 914 such that vertical sliding of the slide plate 914 slides the piston 814 coaxially within the body 812.

The back plate assembly 880 is shown to include an interior plate 924 and a rear cover 926 forming a cavity 928 there between. A motor 930 is schematically shown as provided in the cavity 928 which rotates about axis 931 and output shaft 932 carrying a rotating wheel 934 coaxially with the shaft. A crank pin 936 is mounted at one circumferential location on the wheel. The crank pin 936 is received within a rearwardly opening horizontally extending slot in the slide plate 914. With rotation of the shaft 932 and wheel 934, engagement between the crank pin 936 and the slide plate 914 will cause the slide plate 914 to slide vertically upwardly and downwardly in a reciprocal manner relative to the housing 870.

Within the cavity 928, there is schematically shown the control mechanism 930 and a power source 932. The control mechanism 930 controls the manner of distribution of power to the motor 930 and ozone generator 509. A hand sensing device 940 is provided on the plate 924 as, for example, to sense the presence of a user's hand underneath the discharge outlet 848 of the pump 810 and activate the operation of the pump 810 in known manners. This hand sensing device 940 is also connected to the control mechanism 930. The control mechanism 930 may have various manners for remotely communicating with control systems or other devices and, in this regard, a communication mechanism 934 is shown in the cavity 928 connected to the control mechanism 930 which may comprise various means for wired or wireless communication with external communication devices and controllers such as through preferred WI-FI connections with the Internet and external computerized controls.

The control mechanism 930 in controlling the rotation of the motor 930 controls and is aware of the relative location of the piston 814 relative to the piston chamber-forming body 812. The control mechanism 930 as well controls the generation of ozone generator 509 preferably in a cycle of operation, the control mechanism 930 controls the generation of ozone adequate to provide ozone in the air in a concentration useful for destroying pathogens.

The amount of such ozone in the air is not to be limited, however, preferably, the initial concentration of ozone after generation is at least 0.05% ozone, more preferably, at least 0.1% ozone. As used in this application, the percent of ozone is the volumetric percent of molecules of ozone in the gas at 20° C.

Preferably, in each cycle of operation of a pump, adequate ozone is generated so as to provide the desired levels of ozone in the air in the ozone generating chamber.

The pump assembly 810 comprises two principal elements, a piston chamber-forming member or body 812 and a piston-forming element or piston 814 which has a configuration similar to that disclosed in U.S. Patent Application Publication US 2009/0145296 to Ophardt et al, published Jun. 11, 2009, the disclosure of which is incorporated herein by reference.

Figure 9:
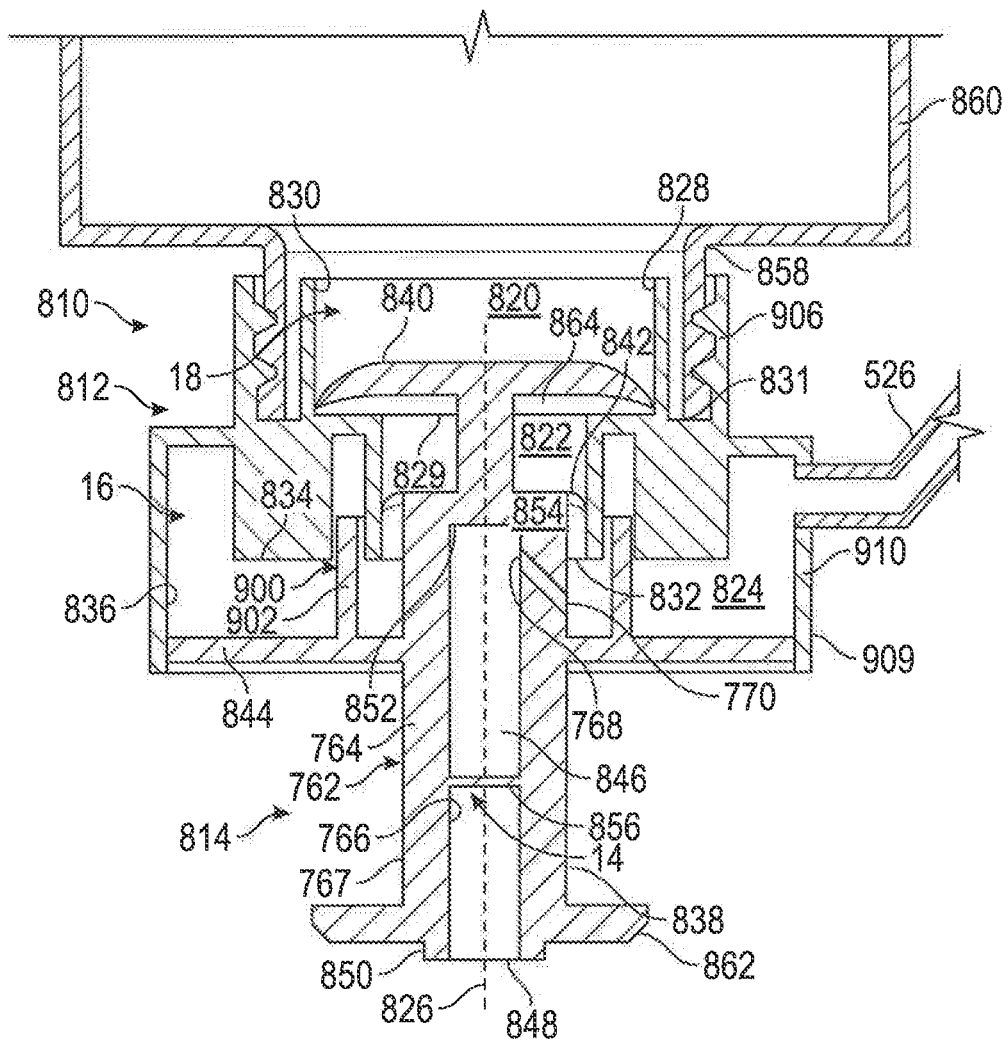
FIG. 9 is an enlarged cross-sectional side view of the dispenser of FIG. 1 as seen in FIG. 1 notably showing the pump assembly.
Figure 10:
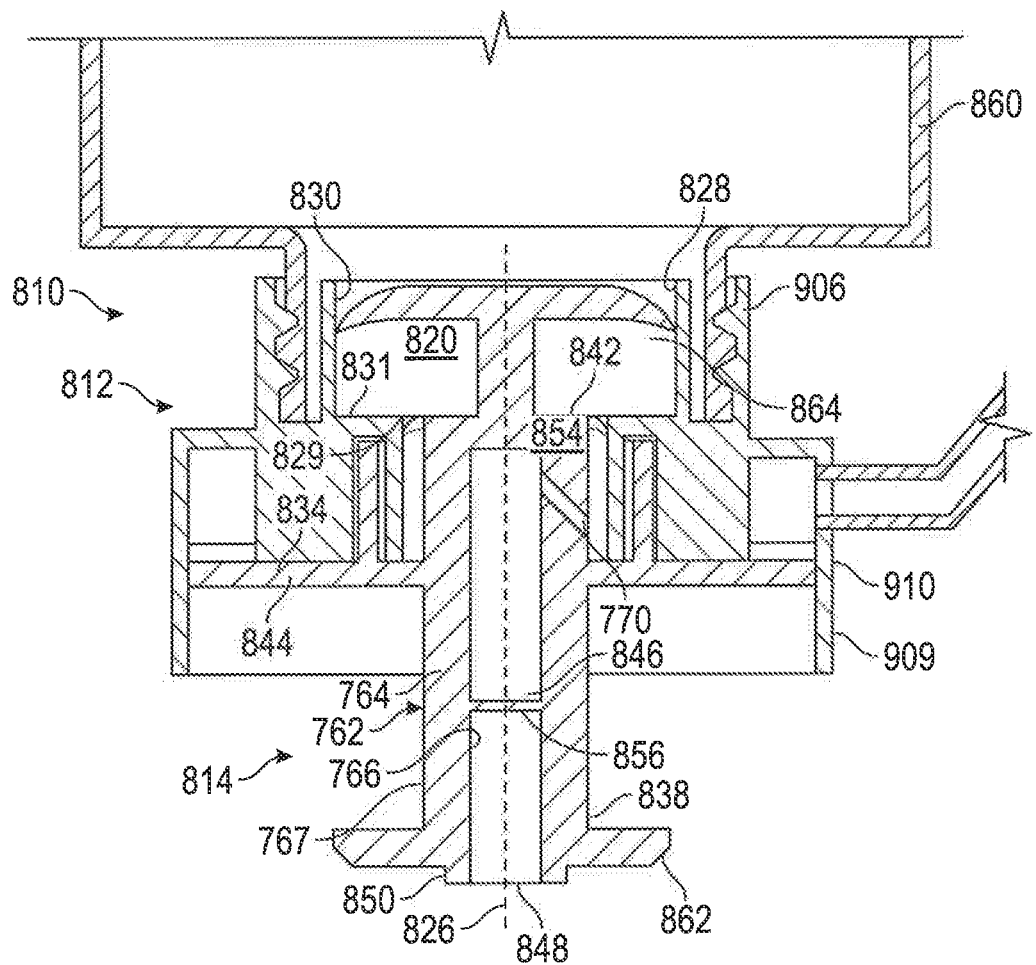
FIG. 10 is an enlarged cross-sectional side view similar to FIG. 9 but showing the pump assembly as seen in FIG. 2.

As best seen in FIGS. 9 and 10 the piston chamber-forming body 812 has three cylindrical portions illustrated to be of different radii, forming three chambers, an inner chamber 820, an intermediate chamber 822, and an outer chamber 824, all coaxially disposed about an axis 826. The intermediate cylindrical chamber 822 is of the smallest radii. The outer cylindrical chamber 824 is of a radius which is larger than that of the intermediate cylindrical chamber 822. The inner cylindrical chamber 820 is of a radius greater than that of the intermediate cylindrical chamber 822 and, as well, is shown to be of a radius which is less than the radius of the outer cylindrical chamber 824.

The inner chamber 820 has an inlet opening 828 and an outlet opening 829. The inner chamber has a cylindrical chamber side wall 830. The outlet opening 829 opens into an inlet end of the intermediate chamber 822 from an opening in a shoulder 831 forming an outer end of the inner chamber 820. The intermediate chamber 822 has an inlet opening, an outlet opening 82, and a cylindrical chamber side wall 833. The outlet opening 832 of the intermediate chamber 822 opens into an inlet end of the outer chamber 824 from an opening in a shoulder 834 forming the inner end of the outer chamber 824. The outer chamber 824 has an inlet opening, outlet opening and a cylindrical chamber side wall 836.

The outer chamber 824 extends axially inwardly and upwardly as shown so as to provide a location for the outlet end 545 of the ozone delivery tube 526 to enter into the outer chamber 824 at all relative positions of the piston 814 in a normal stroke of operation. In this regard, the outlet end 545 of the ozone discharge tube 526 can be seen to open into an annular portion 546 of the cylindrical outer chamber 824.

The piston 814 is axially slidably received in the body 812. The piston 814 has an elongate stem 838 upon which four discs are provided at axially spaced locations. An inner flexing disc 840 is provided at an innermost end spaced axially from an intermediate flexing disc 842 which, in turn, is spaced axially from an outer sealing disc 844. The inner disc 840 is adapted to be axially slidable within the inner chamber 820. The intermediate disc 842 is adapted to be axially slidable within the intermediate chamber 822.

The intermediate disc 842 has a resilient peripheral edge which is directed outwardly and adapted to prevent fluid flow inwardly yet to deflect to permit fluid flow outwardly there past. Similarly, the inner disc 840 has a resilient outer peripheral edge which is directed outwardly and is adapted to prevent fluid flow inwardly yet to deflect to permit fluid flow outwardly there past.

The outer sealing disc 844 is adapted to be axially slidable within the outer cylindrical chamber 824. The outer sealing disc 844 extends radially outwardly from the stem 838 to sealably engage the side wall 836 of the outer chamber 824, and prevent flow there past either inwardly or outwardly. The outer sealing disc 844 carries an upwardly inwardly extending cylindrical tube 900 such that an annular central fluid sump 902 is defined inside the tube 900 between the tube 900 and the stem 838 above outer disc 844. The piston chamber-forming body 812 has an inwardly extending cylindrical recess 904 sized to receive the tube 900 therein but with clearance to provide for fluid passage there between.

The piston 814 essentially forms, as defined between the inner disc 840 and the intermediate disc 842, an annular inner compartment 864, sometimes referred to herein as a liquid compartment or inner liquid compartment, which opens radially outwardly as an annular opening between the discs 840 and 842. Similarly, the piston 814 effectively forms between the intermediate sealing disc 842 and the outer sealing disc 844 an annular outer compartment 866, sometimes referred to herein as an air compartment or an outer air compartment, which opens radially outwardly as an annular opening between the discs 842 and 844.

The stem 838 has an outermost hollow tubular portion 762 with a cylindrical side wall 764 generally coaxially about the central axis 826 defining a central passageway 846 within the tubular portion 762. The central passageway 846 extends from an outlet 848 at the outermost end 850 of the stem 838 centrally through the stem 838 to a closed inner end 852.

The cylindrical side wall 764 of the hollow tubular portion 762 of the stem 838 extends radially of the central axis 826 from an inner side wall surface 766 to an outer side wall surface 767. An inlet passageway 854 provides communication through the stem 838 into the central passageway 846. The inlet passageway 854 extends through the cylindrical side wall 764 from an inner opening 768 in the inner side wall surface 766 to an outer opening 770 in the outer side wall surface 767. The inlet passageway 854 has its outer opening 770 located on the stem 838 in between the outer disc 844 and the intermediate disc 842. The inlet passageway 854 in extending from the inner opening 768 to the outer opening 770 radially outwardly and axially outwardly so as to provide the inner opening 768 located on the stem 838 axially inwardly from the outer opening 770. The inlet passageway 854 extends about an inlet axis extending in a flat plane including the central axis 826 and with the inlet axis in that flat plane extending at an angle to the central axis 826 as the inlet axis extends radially outwardly and axially outwardly.

The inlet passageway 854 has its inner opening 768 at a height above the height of its outer opening 770.

The foam generator 14 is provided including a foam inducing screen 856 is provided in the central passageway 846 intermediate between the inner opening 768 and the outlet 848. The screen 856 may be fabricated of plastic, wire or cloth material. It may comprise a porous ceramic measure. The screen 856 provides small apertures through which an air and liquid mixture may be passed to aid foam production as by production of turbulent flow through small pores or apertures of the screen thereof in a known manner.

The piston 814 carries an engagement flange or disc 862 on the stem 838 outward from the outer sealing disc 844. The engagement disc 862 is provided for engagement by an activating device in order to move the piston 814 in and out of the body 812.

The piston chamber-forming body 812 carries an inwardly directed annular flange 906 which is threaded on a radially inwardly directed surface and adapted to thread ably engage in a sealed manner with the threads on the neck 858 of the container 860. The neck 858 extends downwardly into an outwardly extending annular cavity formed between the flange 906 and a cylindrical portion defining the inner chamber 820.

Figure 2:
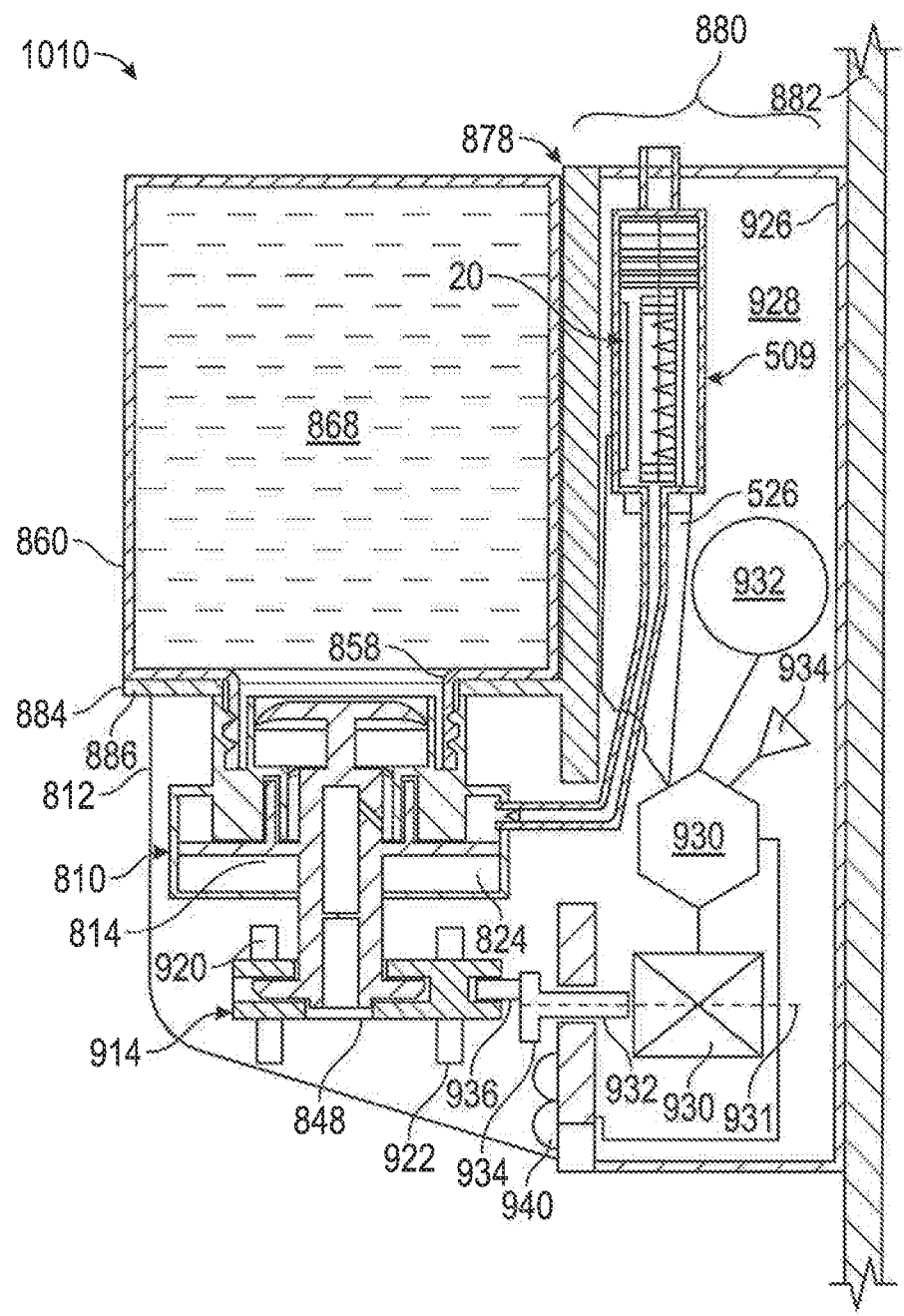
FIG. 2 is a view the same as FIG. 1 but showing the piston pump in a retracted position.

In a withdrawal stroke with movement from a retracted position of FIG. 2 to the extended position of FIG. 1, the volume between the inner disc 840 and the intermediate disc 842 decreases such that fluid is displaced outwardly past the intermediate disc 842 to between the intermediate disc 842 and the outer disc 844. At the same time, the volume in the annular outer compartment 866 between the intermediate disc 842 and the outer disc 844 increases, with such increase being greater than the volume decrease in the annular inner compartment 864 between the inner disc 840 and the intermediate disc 842 such that in addition to the fluid displaced outwardly past intermediate disc 842, what is referred to herein as inhaled material namely air, liquid and/or foam is drawn inwardly via the outlet 848, central passageway 846, and the inlet passageway 854 into the annular outer compartment 866 between the intermediate disc 842 and the outer disc 844.

In a retraction stroke from the position of FIG. 1 to the position of FIG. 2, the volume in the annular outer compartment 866 between the intermediate disc 842 and the outer disc 844 decreases such that what is referred to herein as exhaled material namely air, any ozone generated, liquid and/or foam in the annular outer compartment 866 and in the central passageway 846 above the screen 856 is forced under pressure out through the screen 856. The gas comprising air and any ozone present plus the liquid simultaneously passing through the screen 856 are mixed and commingled producing foam which is discharged out the outlet 848. At the same time, in the retraction stroke, the volume in the annular outer compartment 866 between the inner disc 840 and the intermediate disc 842 increases drawing liquid from inside the fluid containing reservoir or container past the inner disc 840.

Reciprocal movement of the piston 814 between the retracted and extended positions will successively draw and pump precise amounts of liquid from the container and mix such liquid with air drawn from the atmosphere and dispense the liquid commingled with the air as a foam.

Preferably, in the course of one cycle of the piston 814, ozone is generated from oxygen in the ozone generator 509 to create ozonated air which is discharged in the retraction stroke so as to mix with the liquid and form ozonated air-liquid mixture as foam.

In a typical withdrawal stroke, the inhaled material includes ozonated air from the ozone generator 509 and may include drawn back material in the inlet passageway 854 and the central passageway 846, whether inwardly or outwardly of the screen 856, at the end of the last retraction stroke. Such drawback material may typically include foam which substantially fills the central passageway 846 outward of the screen, and foam, liquid and/or air and ozone in the central passageway 846 inwardly of the screen 856 and foam, liquid and/or air and ozone in the inlet passageway 854.

The annular outer compartment 866 is, in effect, a closed bottom compartment forming a major sump whose bottom is defined by the outer disc 844, sides are defined by the side wall 836 and the inner side wall surface 766 of the stem 838 and with an overflow outlet defined by the inner opening 768 of the inlet passageway 854. Within this major sump, the annular central sump 902 is defined within the tube 900 with the sump volume of the central sump 902 being the volume of liquid which may be retained within the tube 900 above the outer disc 844 against over flow out the inlet passageway 854 to the central passageway 846.

In a retraction stroke, the material in the annular outer compartment 866 is forced out of the outer compartment 866 via the outer opening 770 of the inlet passageway 854. In the retraction stroke, the expelled material includes ozonated air and due to a Venturi effect, the air being expelled through the outer opening 770 of the inlet passageway 854 entrains liquid and foam in the central sump 902 in the annular outer compartment 866 and draws the level of material in the sump down typically to the height of outer opening 770 of the inlet passageway 854. Subsequently, in the next withdrawal stroke, the inhaled material is drawn into the annular outer compartment 866 and, simultaneously, a next allotment of liquid from the annular inner compartment 864 is forced from the annular inner compartment 864 past the intermediate disc 842 into the annular outer compartment 866. The inhaled material and the allotment of liquid come to sit in the central sump 902 with the liquid at the bottom of the sump, the foam above the liquid and air above the foam. With the passage of time, foam in the sump will tend to coalesce, that is, separate into air and liquid, with such coalesced liquid increasing the level of liquid in the sump. Insofar as the level of liquid in the central sump 902 is below the inner opening 768 liquid will not flow due to gravity from the outer compartment 866 into the central passageway 846.

Operation of the pump assembly illustrated in FIGS. 1 to 5, 9 and 10 will draw liquid out of the reservoir 860 creating a vacuum therein. The pump assembly 810 is preferably adapted for use with a collapsible reservoir 860. Alternatively, a suitable vent mechanism may be provided if desired as, for example, for use in a non-collapsible container to permit atmospheric air to enter the container 860 and prevent a vacuum being built up therein.

In the dispenser of FIGS. 1 and 2, by rotation of the motor 930, the piston 814 is moved in a cycle of operation between a withdrawn position shown in FIG. 1 and a retracted position shown in FIG. 2.

Preferably, in operation of the dispenser 1010 of FIGS. 1 and 2, during rest periods at times when the dispenser is not in use, the control mechanism 930 will maintain the piston 814 in the retracted position as seen in FIG. 1. On the dispenser 1010 sensing the presence of a user's hand under the discharge outlet 848, the control mechanism 930 will then move the piston 814 to the extended position and, in so doing, draw ozone from the ozone generator 509, subsequently moving the piston 814 to the retracted position so as to dispense foam containing ozone onto the user's hand.

In the preferred embodiment, the passageway for the ozonated air, notably provided by the ozone discharge tube 526, leads downwardly to the bottom of the ozone generator 509 to the outer chamber 824 and is believed to be advantageous such that ozone, which is heavier than air, will have a tendency to concentrate in the lowest-most portion of the passageway, and to flow towards the outer chamber 824.

The ozone generator 509 preferably has an ozone generating capacity sufficient to generate adequate ozone for use of the dispenser under varying conditions.

Methods of operation of the ozone generator 509 to provide adequate ozone include operation to provide "on demand" generation of ozone, operation to provide a pre-existing "reserve supply" of ozone, and combinations thereof.

In a preferred embodiment for an "on demand" method for generating ozone, the ozone generator may have sufficient capacity for generating ozone with time that the ozone generator 509 can generate sufficient ozone for a single activation of the pump during the time that the pump moves in a cycle of operation and move preferably with a piston pump during a charge stroke that ozonated air is drawn into the pump chamber as in the withdrawal stroke in the embodiment of FIG. 1 in which the piston is moved from its retracted position to its extended position. With many piston pump dispensers of the type illustrated in this invention, the time of a complete cycle in dispensing is, for example, about one second with the time of a withdrawal stroke being about half a second and the time of a retraction stroke being about half a second. Preferably, the ozone generator 509 of FIGS. 1 and 2 may have a capacity to generate ozone such that, for example, in a half second, adequate ozone is generated at least equal to the amount of ozone that has been drawn from the ozone generator in a single stroke of operation.

One method of operation which can assist "on demand" creation of adequate ozone with an ozone generator having a small capacity as possible is such that after the hand of a user being sensed under the discharge outlet that there is an increased time period for the ozone generator 509 to generate ozone before the end of the charge stroke drawing ozonated air into the outer chamber of the pump.

This increased time could be arranged for by providing a time delay after sensing the user's hand and initiating movement of the piston from the retracted position. However, a time delay in which no operation of the dispenser is sensed by a user is often disturbing to a user. Rather than have a time delay in operation, the pump in FIG. 34 may be controlled such that the time for the charging withdrawal stroke is greater than the time for the discharging retraction stroke. For example, rather than have the time of the withdrawal stroke be equal to the time of the retraction stroke, which is a typical arrangement, the withdrawal stoke could be longer in time as, for example, with a ration of time of withdrawal stroke to time of retraction stroke being in the range of 5:4 to 3:1, more preferably about 2:1. The overall time of a cycle of operation could be increased as well, however, it is preferred if a stroke does not exceed about 1 second or 1.5 second. As one example, the length of a cycle is maintained as about 1 second with the withdrawal stroke increased as to about ⅔ of a second and the discharge stroke reduced to about ⅓ of a second.

The control of the relative time duration of the withdrawal stroke and the retraction strokes can be accomplished various ways. As examples, the speed of rotation of the motor can be varied in each cycle and the nature of the mechanical linkage coupling the actuator slide plate 914 to the motor may be selected to provide different strokes with constant speed of rotation of the motor.

Preferably, the dispenser may be designed with the ozone generator 509 to have low electrical consumption to conserve power particularly so that the dispenser may be battery powered or powered by electricity created by a manually operated generator. Preferably, the ozone generator 509 may have a relative small volumetric size so as to not unduly increase the size of the dispenser or reduce the size of a fluid containing reservoir for the dispenser. These preferred constraints on electrical consumption and size lead towards adopting a generator with merely enough capacity to generate an amount of ozone with time which can merely meet typical demands on the dispenser.

Another method of operation which provides for increased time to generate ozone before the end of a charging stroke is to commence generation of ozone before a user's hand is sensed under the piston 810.

Referring to FIG. 1, the dispenser is shown as including in addition to the hand sensing device 940, a secondary person sensing device 941 for preferred, albeit optional, use in a manner now described. In accordance with the various embodiments of the invention, the hand sensing device 940 is preferably adapted to sense the presence of a user's hand disposed below the piston 810. FIG. 1 schematically illustrates the hand sensing device 940 as adapted to determine whether or not a person's hand may be disposed as, for example, at a location 942 marked on FIG. 1 substantially directly below the piston 810. The secondary sensor 941 may preferably be adapted to sense the location of a person's hand or the user at a location spaced from the dispenser as, for example, one foot or two feet or three feet spaced forwardly from the dispenser and schematically illustrated as a location 943. The secondary person sensing device 941 can be used towards sensing the approach of an expected user to the dispenser and thus provide a signal indicating the user of the dispenser at a time period before a time when the hand sensing device 941 senses the position of a person's hand underneath the piston 810. This advance warning that a user will use the dispenser may be used as an input to the control mechanism 930 so as to have the control mechanism 930 direct the ozone generator 509 to commence generating ozone at a time earlier than would result if a request for generating ozone was not initiated until the user's hand is sensed underneath the piston by the hand sensing device 940. This advance notice that a user is to use the dispenser and earlier initiation of generation of ozone with the ozone generator can be of assistance towards ensuring that there will be adequate ozone in the ozone generator to be drawn by the piston pump in an initial withdrawal stroke from the position of FIG. 2 to the position of FIG. 1. For example, this may be advantageous if, for example, the capacity of the ozone generator 509 to generate ozone may be limited. Rather than provide two different sensing devices 941 sensors 940 and 941, a single sensing mechanism may be used which has a capability of sensing the presence of a user at different locations. Pairs of sensors of the type disclosed in U.S. Patent Publication US 2009/0045221 to Ophardt, published on Feb. 19, 2009, may be used.

As contrasted with the "on demand" methods of control of the ozone generation, another method is to maintain a supply of ozonated air in the ozone generator 509 ready to be used, and to replenish this supply by generating more ozone when ozonated air is withdrawn. In such an arrangement, the ozone generator 506 need not have a capacity to generate adequate ozone in the same time as a charging withdrawal stroke and, for example, replenishment could be adequate if the ozone generator created adequate ozone for replenishment in the time of a full cycle, for example, one second of generation of ozone for a one second cycle of pump operation. However, since there may on average be expected to be a greater time period between activations of the dispenser by different users than merely time of one cycle of operation, the ozone generator could have a capacity to generate adequate ozone for a single cycle in a time greater than the time of the single cycle, for example, in the time of two, three or four cycles.

The ozone generator 509 could also be controlled in a manner that there is constantly adequate ozone within the ozone generating chamber 516 for at least one cycle of operation of the pump and, more preferably, two, three or more cycles of operation of the pump.

Ozone has a tendency to revert back to oxygen over time. Thus, within the ozone generator, ozone that may be generated within the corona discharge chamber 516 will, after time, revert back to being oxygen. Under typical temperature and relatively low humidity conditions, the half-life of ozone may be approximated as thirty minutes. The half-life is the time that it takes for half of the ozone to revert to oxygen.

Preferably, the control mechanism 930 controls operation of the ozone generator 509 by estimating the ozone in the ozone generator at any time having regard to one or more of: monitoring of the number of activations of the pump, estimating the amount of ozone generated in the ozone generator 509 over time having regard to factors including the output information from the sensor mechanism 20, estimating the amounts of ozone withdrawn by the activations of the pump, monitoring time and estimating the amount of ozone in the ozone generator which has reverted to oxygen over time. The control mechanism 930 can direct the ozone generator 509 to generate ozone from time to time as may be required so as to maintain the ozone concentration within the ozone generating chamber 516 within pre-established limits to assist in ensuring that there is adequate ozone in the ozone generating chamber 516 for at least one and possibly a number of activations of the pump.

As one example, an ozone generator was selected to produce adequate ozone for a simple cycle of operation of the piston pump during that cycle of operation. An ozone generator with an internal volume of 35 ml has been tested in a dispenser as illustrated in FIG. 35 which generates adequate ozone in ½ second for a typical single dose of foaming liquid of 1.0 ml dispensed in a volume ratio of liquid to ozonated air of 1:15 and in which the ozonated air has a concentration of about 0.05% by volume ozone. This tested ozone generator was used to supply ozone to a piston pump with initiation of generation of ozone by the generator to coincide with the initiation of the withdrawal stroke and the ozone generator to generate ozone for ½ second during the withdrawal stroke. The discussion of the control of generation of ozone has been principally directed to a discussion in the conduct of a piston pump as illustrated in FIG. 1 in which ozone is charged into the pump chamber in a withdrawal stroke. Of course, other piston pumps could be selected in which ozone is charged into the pump chamber as the piston is retracted. In either case, on demand ozone generation is preferred during a charge stroke when ozone is drawn into the pump.

The control mechanism 930 is also to be operated in a manner so as to maintain an adequate concentration of ozone in air in the ozone generating chamber having regard firstly to the natural decomposition of ozone into oxygen with the passage of time and having regard to the time that has passed since the pump was first operated in the cycle of operation to dispense air. For example, if some time has passed since the pump was last cycled, the control mechanism 930 may generate additional ozone at periodic intervals so as to replace ozone in the ozone generating chamber which has decomposed back into oxygen. For example, if there is no operation of the pump, then ozone may again be generated every fifteen minutes or every half hour.

During the period of time when the dispenser is not expected to be used, then the control mechanism 930 can, for example, discontinue the generation of ozone and with knowledge that it has discontinued generation of ozone, if the pump mechanism 810 is to be cycled when the ozone would be depleted in the, the control mechanism could ensure that adequate ozone is generated before the dispenser is permitted to be cycled. The control mechanism may be able to generate ozone in a significantly small period of time as by increasing the energy supplied to the ozone generating mechanism.

As to the power supply 932 which may be used, the power supply may comprise permanent hardwired AC electrical supply or, for example, replaceable batteries.

In use of the dispenser 1010, once exhausted, the empty, collapsed reservoir 860 together with the attached pump 810 are removed and a new reservoir 860 and attached pump 810 may be inserted into the housing. Preferably, the removed reservoir 860 with its attached pump 810 are both made entirely out of recyclable plastic material which can easily be recycled without the need for disassembly prior to cutting and shredding.

It is to be appreciated that in the first embodiment of FIGS. 1 to 5, the inner disc 840 and the intermediate disc 842 form a first stepped pump and, similarly, the intermediate disc 842 and the outer disc 844 form a second stepped pump. The first pump and second pump are out of phase in the sense that in any one retraction or extension stroke while one pump is drawing fluid in, the other is discharging fluid out. This is not necessary in accordance with the present invention.

Figure 6:
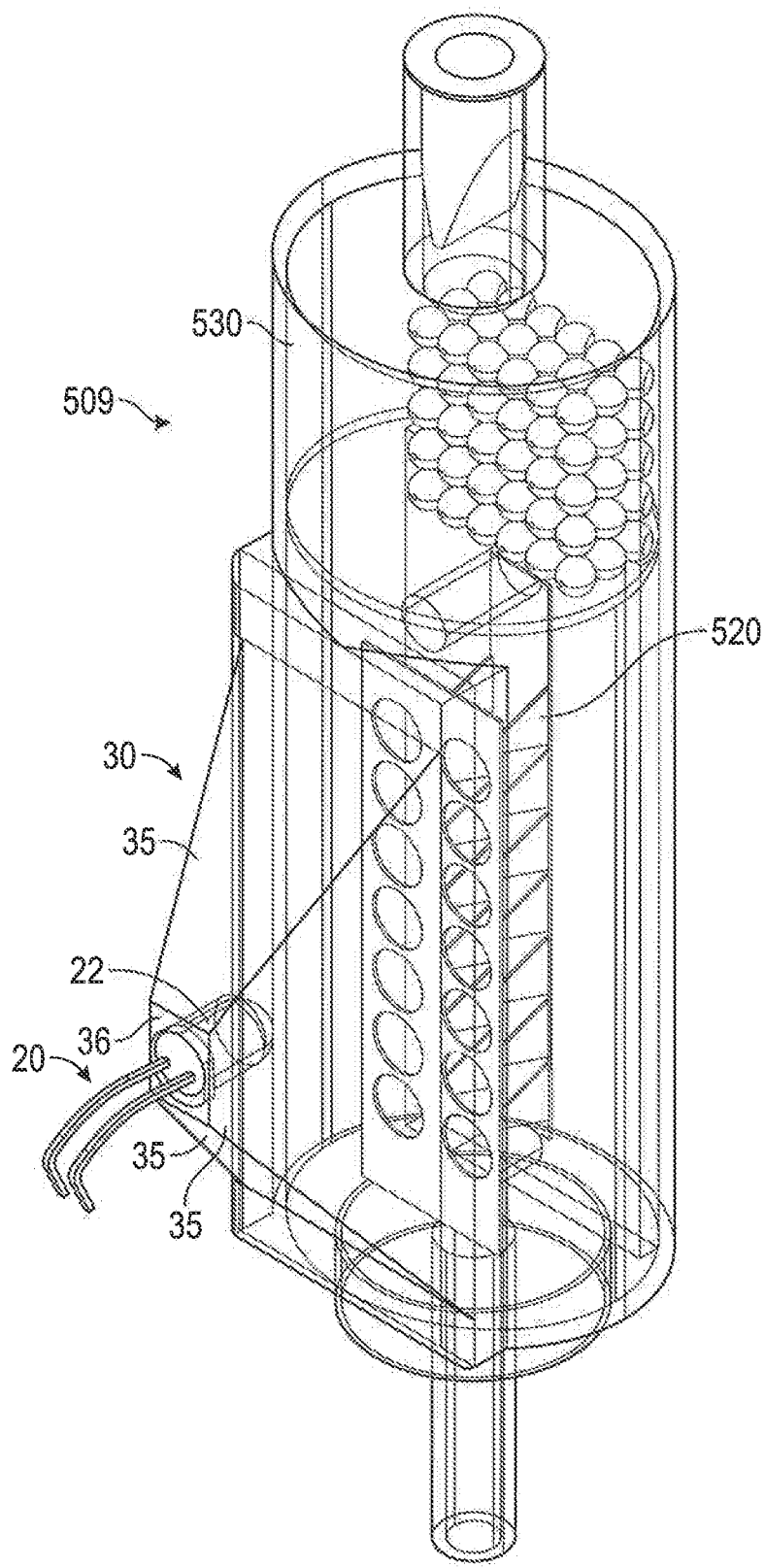
FIG. 6 is an enlarged pictorial view of a second embodiment of an ozone generator with a corona discharge mechanism for use in substitution into the dispenser of FIGS. 1 and 2 in replacement of the first embodiment the ozone generator in FIGS. 1 to 5.
Figure 7:
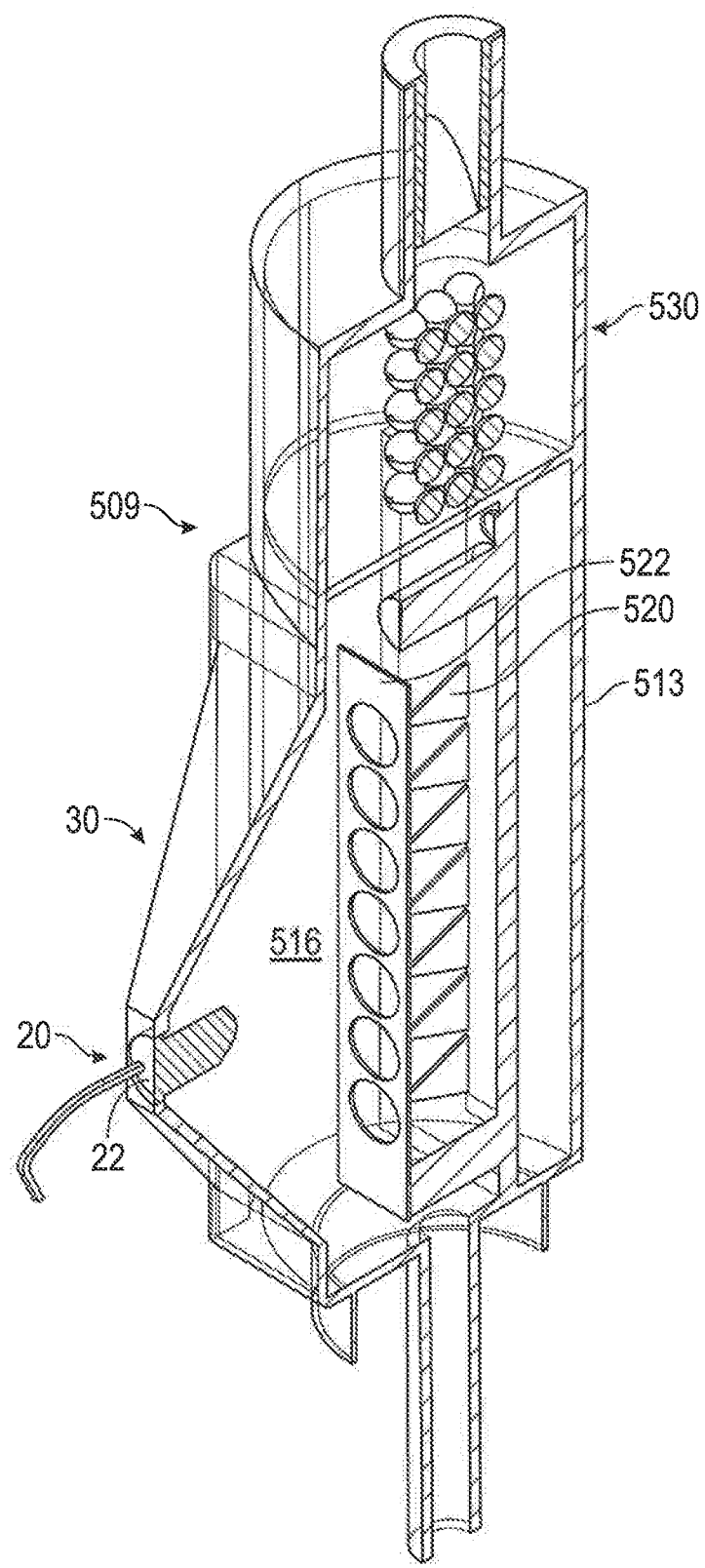
FIG. 7 is a cross-sectional side view of the ozone generator in FIG. 6.
Figure 8:
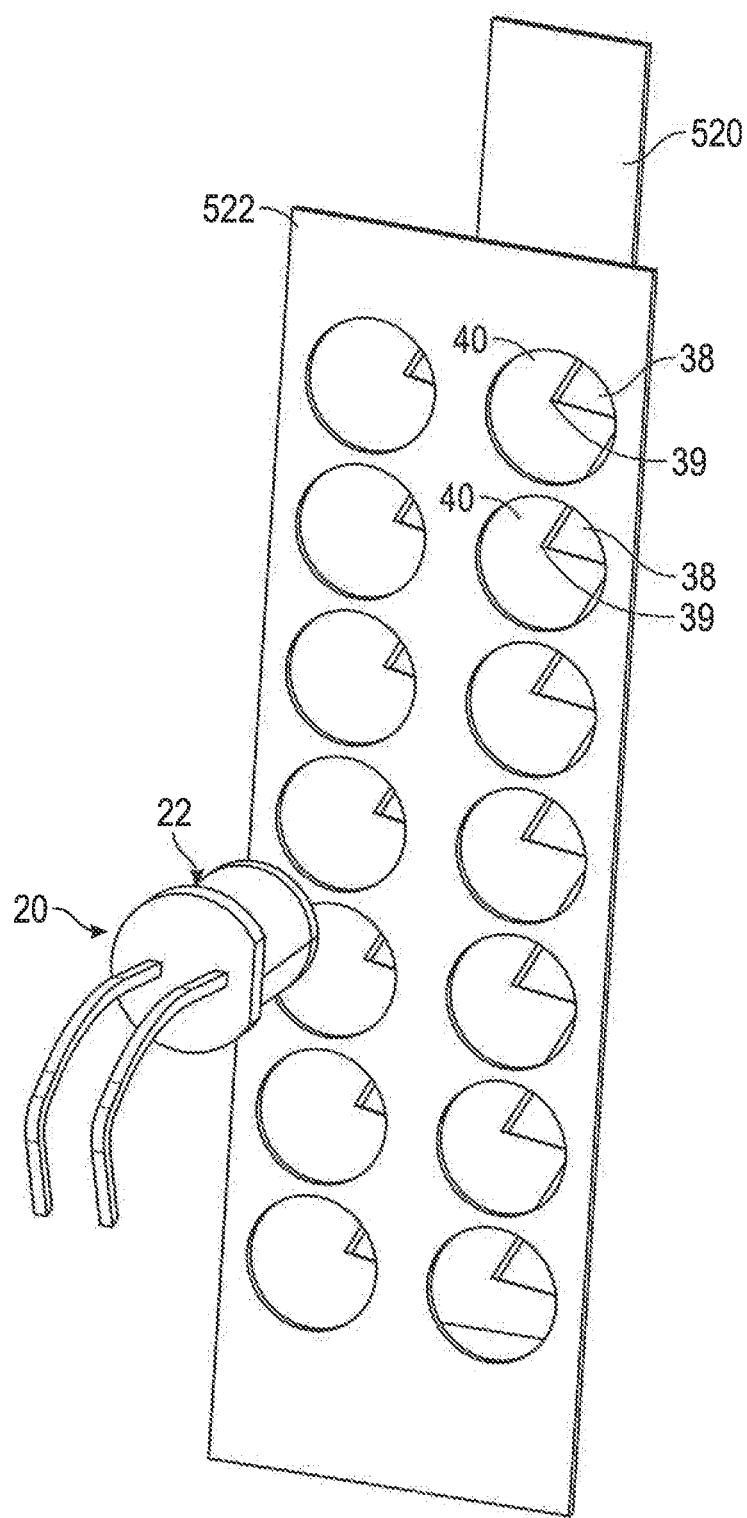
FIG. 8 is a schematic pictorial view showing the sensor and the spaced electrodes of the corona discharge mechanism in FIGS. 6 and 7.

Reference is made to FIGS. 6 to 8 which show a modified form of the ozone generator 509 shown in FIGS. 1 to 5 and which is useful for replacement of the ozone generator 509 shown in FIGS. 1 to 5. The ozone generator 509 in FIGS. 6 to 8, however, is adapted for use with a sensor mechanism 20 that comprises but a single sensor 22. To assist in the single sensor 22 in sensing parameters that arise within the ozone generating chamber 516, the cylindrical outer wall 513 of the housing 530 has been modified so as to provide a funneling manifold 30 that extends radially outwardly and provides, as best seen in FIG. 7, the individual sensor 22 as received in a position that a single sensor 22 may direct and receive the electromagnetic radiation and sound from the ozone generating mechanism. The funneling manifold 30 can be seen to have four pyramid forming side walls 35 which funnel to a flat end wall 36 within which the sensor 22 may be removably secured in a sealed fashion for insertion and removal from the exterior of the housing 530.

As can be seen in FIGS. 6 to 8, the first electrode 520 has a plurality of tapering metal spikes 38 that lead to a distal spike end 39 which are located centered rearwardly from the second electrode 522 relative one of the plurality of circular openings 40 through the second electrode 522. The single sensor 22 is located within the funneling manifold 30 in a manner that there is a direct straight line of sight from the spike end 39 of each of the metal spikes 38 on the first electrode 520 through the openings 40 in the second electrode 522 to the sensor 22, as is believed to be advantageous but is not necessary.

Figure 11:
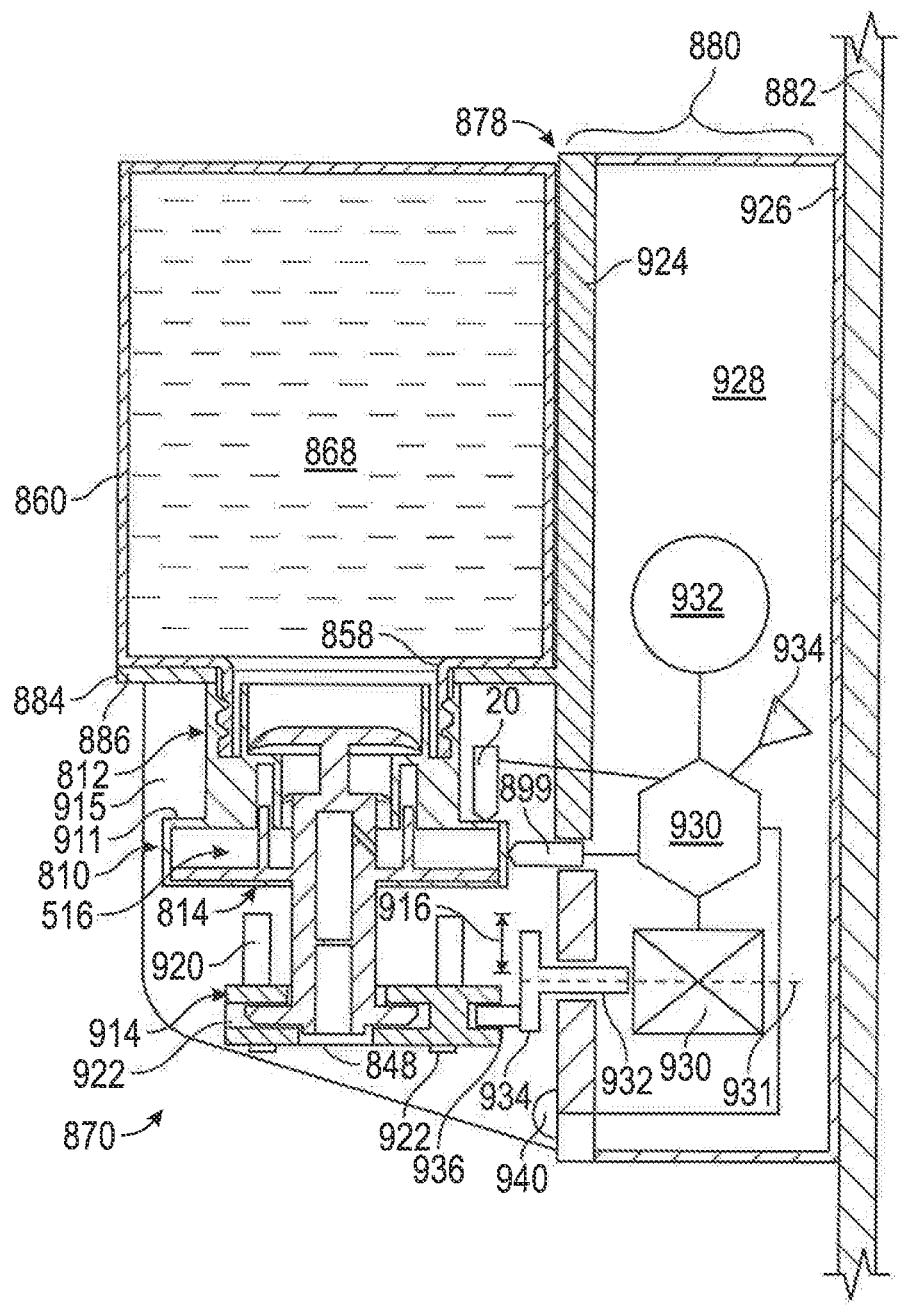
FIG. 11 is a schematic cross-sectional side view of a second embodiment of a dispenser comprising an automated dispenser for dispensing ozone foam using an ozone generator having an ultraviolet emitting mechanism.

Reference is made to FIG. 11 which shows a second embodiment of a dispenser in accordance with the present invention. The second embodiment has many similar elements to those in the first embodiment and similar reference numerals refer to similar elements. A notable difference, however, is that in FIG. 11, ozone generation is achieved by providing ultraviolet radiation emitter mechanism 899 to irradiate atmospheric air within the outer chamber 824 defined within the pump assembly 810, and the separate ozone generator 509 shown in the first embodiment of Figure s 1 to 5 is not provided.

FIG. 11 shows the ultraviolet radiation emitting mechanism 899 as being positioned proximate an exterior surface 909 of a wall 910 of the body 812 within which the outer chamber 824 is defined. The emitting mechanism 899 is adapted to emit ultraviolet radiation radially through this wall 910 into the outer air compartment 866 so as to generate ozone in the outer compartment 866 by converting oxygen of the air within the outer compartment 866 into ozone. The outer air compartment 866 effectively forms an ozone generating chamber 516. The emitting mechanism 899 is preferably operated in a controlled manner such that ultraviolet radiation is emitted into the air compartment 866 at times when the ultraviolet radiation emitted will impinge upon air within the outer air compartment 866. Thus, for example, it is preferable to emit radiation via the emitting mechanism 899 into the air compartment 866 as when the air compartment 866 contains air as, for example, when the outer disc 844 is in a position below the emitter 899, such as when the piston 814 is in the fully extended position as shown in FIG. 9 and positions reasonably proximate thereto such as in positions in which the piston 814 is closer to the extended position shown in FIG. 9 than to a retracted position.

The emitting mechanism 899 may be controlled in a manner to be operated to emit radiation provided that any radiation emitted will reasonably impinge upon air within the air chamber 866.

In FIG. 11, a sensor mechanism 20 is provided to sense parameters within the ozone generation chamber 516. The sensor is illustrated as a single sensor disposed such that it can sense a parameter within the ozone generation chamber 516. In FIG. 11 with the ozone generator mechanism comprising an ultraviolet emitter, the sensor mechanism 20 is adapted to sense one or more parameters selected to be a relatively easily sensed parameter that bears a relationship with the amount of ozone produced. The applicants have appreciated that parameters that bear a relationship with the amount of ozone produced with an ultraviolet emitter as the ozone generating mechanism preferably comprise electromagnetic radiation produced by the emitting mechanism 899. The sensor mechanism 20 in sensing the actual amount of ultraviolet radiation within the ozone generating chamber 516 can provide a more accurate representation of the amount of ozone being produced as contrasted with, for example, using electrical inputs directed to the emitting mechanism 899 to determine ozone generated.

One emitting mechanism 899 is shown in solid lines in FIG. 11 as emitting radiation radially into the ozone generation chamber 516 formed by the air compartment 866. Air within the ozone generation chamber 516 may be irradiated by radiation from an emitter of the emitting mechanism 899 directed at any direction. The wall of the air compartment 866 through which radiation from the emitting mechanism 899 is to emit radiation needs to be formed of a material which permits the radiation emitted to pass therethrough. While the entire wall 910 circumferentially entirely about the axis 826 may transmit radiation, merely a window portion of the wall 910 may permit radiation to pass therethrough and thus form a window for radiation to be orientated aligned with the emitter of the emitting mechanism 899.

While a portion of the wall 910 may be adapted to permit radiation to pass therethrough into the air compartment 866 forming the ozone generation chamber 516, it is also within the scope of the invention that other portions of the wall 910, the body 812 and piston 814 defining the air compartment 866 and the ozone generation chamber 516 be provided so as to not transmit ultraviolet radiation therethrough thus, for example, serve to entrap radiation therein by reflecting radiation back into the ozone generation chamber 516 or, alternatively, absorbing radiation against its transmission as to a user or other portions of the dispenser where it is not desired. The dispenser 870 may have protective covers or shrouds (not shown) to prevent radiation from being transmitted out of the ozone generation chamber 516 as, for example, a protective cylindrical radiation impermeable or reflective shroud which might encircle the pump assembly 810 outside of the reservoir when the pump assembly is installed on the dispenser 870.

The preferred embodiment shows in FIG. 11 one arrangement of piston pump useful in arrangement for generating ozone internally within a variable volume air compartment 866 forming the ozone generation chamber 516 within the pump. However, particular configurations of pumps which can be used for generation of ozone therein is not limited to this embodiment. For example, in any of the various pumps shown in the following U.S. patents may be useful for creation of ozone by a radiation of the air within the air chambers formed therein: U.S. Patent Application Publication US 2009/0145296 to Ophardt, published Jun. 11, 2009; U.S. Patent Application Publication US 2006/0237483 to Ophardt, published Oct. 26, 2006; and U.S. Pat. No. 6,409,050 to Ophardt, issued Jun. 25, 2002, each of which is incorporated herein by reference.

The embodiment of FIG. 11 illustrates an ozone generator using an ultraviolet emitting mechanism for generating ozone within the ozone generating chamber 516 formed within the outer chamber 824 defined within the pump assembly 810. While not shown in the drawings, in addition to the ozone generator provided within the pump assembly 810, a separate ozone generator of the type illustrated in FIG. 1 could be provided to deliver air into the outer chamber 824 as in the manner of FIG. 1 and thus provide two separate ozone generators.

Figure 12:
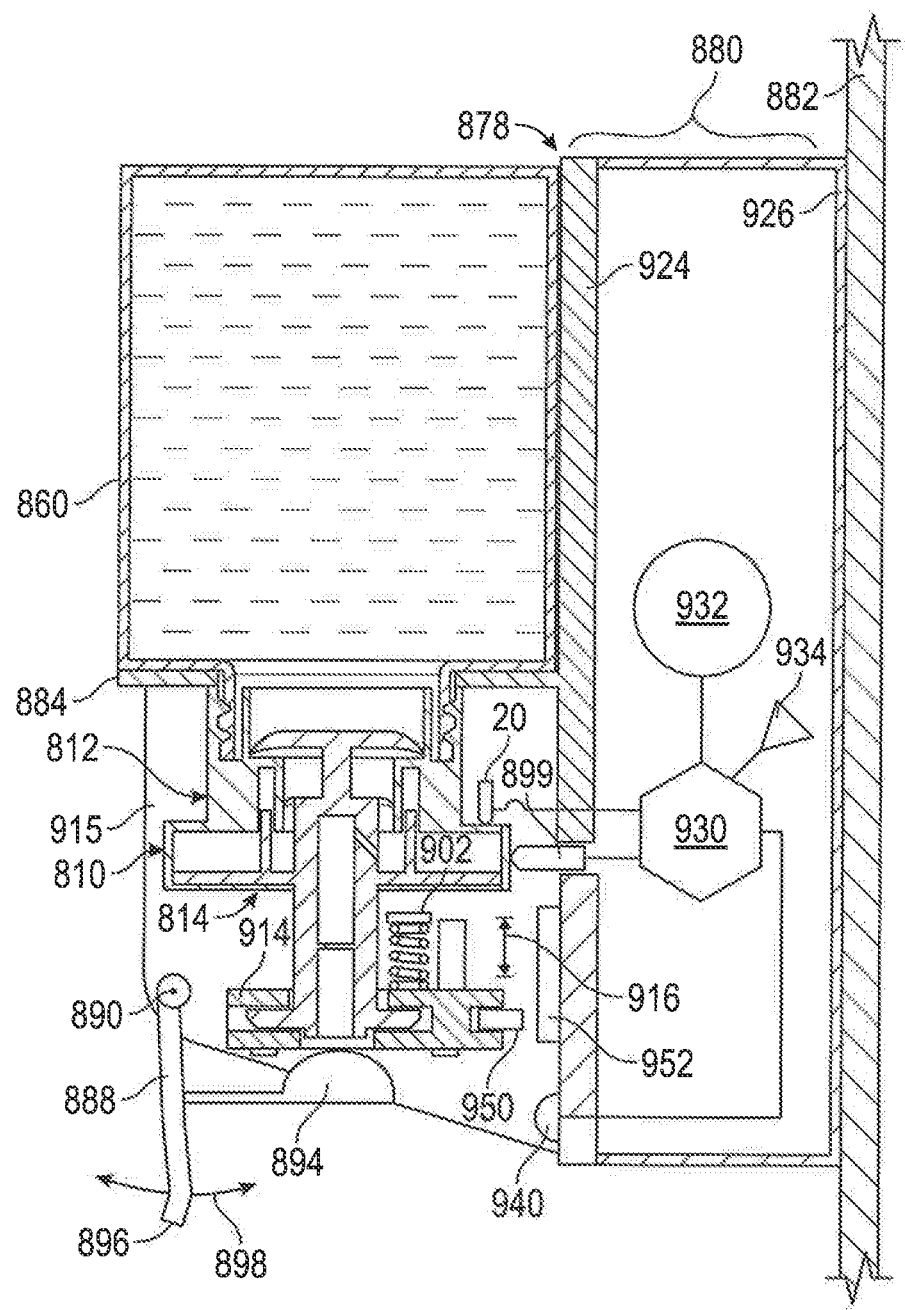
FIG. 12 is a schematic cross-sectional view of a third embodiment of a dispenser comprising a manually operated dispenser for dispensing an ozone foam using an ozone generator having an ultraviolet emitting mechanism.

Reference is made to FIG. 12 which illustrates a tenth embodiment of a dispenser which is adapted to be manually operated. The manually operated dispenser of FIG. 12 is substantially identical to the automated dispenser shown in FIG. 9 with the exception that the motor, its shaft, wheel and crank pin are removed. As in FIG. 11, the sensor mechanism 20 is provided to sense a parameter within the air compartment 866 forming the ozone generation chamber 516 and provide output information to a control mechanism 930.

In the manually operated embodiment of the dispenser of FIG. 12 between the side plates 915 of the dispenser, there is carried at a forward portion an actuating lever 888 journaled for pivoting about a horizontal axis at 890. The lever 888 carries an arm 894 to engage the actuator slide plate 914 such that manual movement of the lower handle end 896 of lever 888 towards the right in the direction indicated by arrow 898 slides the slide plate 914 and therefore piston 814 inwardly in a retraction pumping stroke. On release of the lower handle end 896, a spring 762 disposed between the housing 878 and the slide plate 914 biases the slide plate 914 downwardly to move the lever and the piston 814 to the fully withdrawn position seen in FIG. 26.

The slide plate 914 is adapted to permit manual coupling and uncoupling of the piston 814 as is necessary to remove and replace reservoir 860 and pump assembly 810.

The manually operated embodiment in FIG. 12 continues to have the control mechanism 930, power source 932, communication unit 934 and sensor 940 as in the embodiment of FIG. 11. While not necessary, to assist the control mechanism 930 in controlling the operation of the pump assembly 810, preferably a mechanism is provided whereby the control mechanism 930 will know the relative position of the piston 814 in the body. This, for example, can be accomplished by a magnet 950 carried in the slot of the slide plate 914 whose position may be sensed by a magnetic sensor or sensors 952 carried on the interior plate 924 and coupled to the control mechanism 930.

The manual movement of the lever 888 may be utilized to generate electrical energy in an electrical generator in the same manner as, for example, in U.S. Pat. No. 8,733,596 to Ophardt, issued May 27, 2014, the disclosure of which is incorporated herein by reference. The electrical energy generated may power the manual embodiment in creating ozone and its other functions.

Other mechanisms for moving the piston 814 as shown in FIGS. 11 and 12 can be provided including other mechanized and motorized mechanisms.

Figure 13:
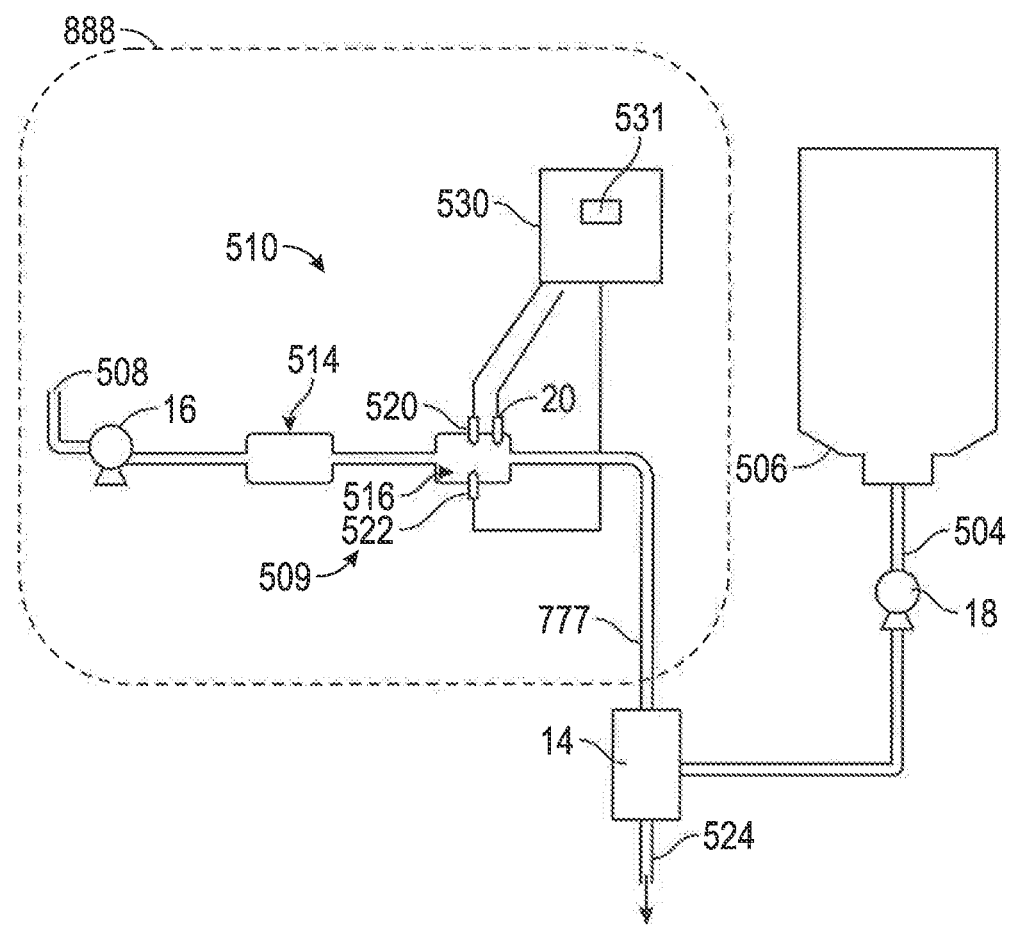
FIG. 13 is a schematic cross-sectional side view of a fourth embodiment of a dispenser for generating ozone and dispensing an ozone foam.

Reference is made to FIG. 13 which shows a fourth embodiment of a dispenser 510 in accordance with the present invention. The dispenser 510 includes an air pump 16. The air pump 16 has an air inlet 508 in communication with atmospheric air, however, with the atmospheric air to be drawn into air pump 16 to pass from the air inlet 508 through a desiccant air filter 514 which serves to remove moisture from the air and then through an ozone generating chamber 516 of an dielectric ozone generator 509 and, hence, to the pump air inlet 500. The dielectric ozone generator 509 has a dielectric discharge mechanism with two electrodes 520 and 522 and air passes through the ozone generating chamber forming ozone from oxygen in the air. The air pump 16 serves to pass air through the ozone generator 509 and to deliver ozonized air to a foam generator 14. A liquid pump 18 has a liquid inlet 504 in fluid communication with fluid from a soap reservoir 506, the liquid pump 18 discharges liquid from the reservoir 506, to the foam generator 518. The ozonized air and liquid mix in the foam generator 14 with the result that a foam is dispensed out the foam out outlet 524.

In FIG. 13, the air pump 16 is shown as upstream of the ozone generator 509, however, the air pump 16 may be provided to be downstream. The nature of the air pump 16 is not limited to being a piston pump and may comprise any manner of air pump or air delivery system.

As in the other embodiments, in FIG. 13 the ozone generator 509 includes a sensor mechanism 20 to sense at least one parameter indicative of the ozone generation in the ozone generator 509 with time and this sensor mechanism 20 provides input to a control board 530 of a control mechanism for control of the ozone generator 509, as well as, preferably, the operation of the air and liquid pumps and the overall operation of the dispenser. The control board 530 preferably includes a processor 531 to receive an output from the sensor mechanism 20 representing the parameter sensed with time and to estimate the amount of ozone generated with time as a function of the parameter sensed by the sensor mechanism 20. The processor 531 is to receive an output from the sensor mechanism 20 representing the parameter sensed with time and to estimate the amount of ozone generated with time as a function of the parameter sensed by the sensor mechanism 20 could be provided remote from the dispenser as with the output information from the sensor mechanism 20 communicated to a remote computer or controller.

In the fourth embodiment of FIG. 13, the air pump 16, the ozone generator 509 and the control board control board 530 provide an ozone containing gas generator 888 for delivery of ozonated gas from an outlet indicated by conduit 777. In FIG. 13, each of the foam generator 14, the liquid pump 18, and the soap reservoir 506 could be eliminated such that the ozone containing gas generator 888 would provide ozonated gas for any use desired as controlled, amongst other things, with the input from the sensor mechanism 20. The invention also provides the combination of merely the ozone generator 518 with the sensor mechanism 20 as a novel ozone generator, as well as a method for generation of ozone using the ozone generator by control of the ozone generator with feedback from the sensor mechanism 20.

In accordance with some embodiments of the present invention, a foam liquid product is provided dispensed from the outlet of the dispenser in which air within the bubbles in the foam includes ozone within a concentration effective for various purposes including, notably, cleaning, disinfecting and, preferably, killing pathogens. In accordance with the present invention, it is preferred that the liquid which is to foam and form the bubbles to contain the ozonated air may be a cleaning fluid, however, this is not necessary. The liquid which is to foam and form the bubbles to contain the ozonated air may merely serve the purpose of a carrier for the ozonated air. Preferably, the bubbles of the foam may remain unbroken for a period of time that the ozone may be delivered to where cleaning or disinfecting is desired as, for example, on all and various different surfaces of a person's hand or to surfaces which are to be cleaned. Preferably, the foam containing ozone will have bubbles with a tendency to remain unbroken for a period of time preferably of at least one second, or two seconds or three seconds or five seconds or ten seconds or more to assist in providing adequate time for the foam after generation to be applied to surfaces to which it is to clean or disinfect.

The relative ratios of gas to liquid which may comprise the bubbles of the foam may be varied depending upon the nature of the liquid and the desired purposes of the foam.

Many typical foaming liquids with cleaning properties are known and which can be foamed with the volume of liquid injected relative to the volume of air injected being in the range of about 1 to 10 to 1 to 15. Such relative ratios are also suitable for use with ozonated air. Advantageously, the relative volumes of liquid to air containing ozone may be greater as, for example, in the range of about 1 to 15 to 1 to 50 or 1 to 60 as may be desired. Such an ozonated air containing foam with a low relative amount of liquid can be advantageously used as a vehicle to provide cleaning or disinfecting effective levels of ozone on surfaces to be cleaned. In accordance with the present invention, there is provided a particularly useful foam product having liquid to gas ratios in the range of 1 to 10 to 1 to 60 and, preferably, with half-life times for the foam, defined as the time in which half of the foam bubbles become broken, being in the range of three seconds to thirty seconds or longer. Such foams can serve as an advantageous vehicle for delivering ozone into any environment which is desired to be cleaned including a person's hands, articles, walls, a toilet bowl and, as well, wounds, sores, burns or other openings in a human or animal body.

Ozone is soluble in water. During the mixing of the ozonated air and liquid to form the foam, the ozone within the ozonated air will have a tendency to become dissolved in the liquid, particularly if it is water based or to react with the liquid or components of the liquid since ozone is a strong oxidizing agent. Ozonated water is useful as a cleaner and sanitizer.

A resultant foam product can provide for advantageous cleaning by reason of both the delivery of ozonated air in the foam bubbles and by reasons of the delivery of ozonated liquid preferably ozonated water. The liquid used to make the foam preferably is selected to minimize reaction with ozone which reduces the ozone concentration in the ozonated air or the liquid. The particular foaming agents used in the foaming liquid preferably are agents which do not react with ozone.

The foam provides an excellent high liquid to air surface area for transfer of ozone from the ozonated air into the liquid of the foam.

With knowledge of the extent to which ozone will be dissolved into the liquid, the concentration of ozone in the ozonated air may be selected to provide for a resultant foam with advantageous ozone dissolved in the liquid of the foam and ozone remaining in the air of the foam bubbles for cleaning and disinfecting purposes as desired.

As a pump assembly for dispensing a fluid, the preferred embodiments illustrates the use of a piston type pump. The invention is not so limited that any manner of fluid discharge mechanism may be suitable when the product is a fluid including, for example, rotary pumps, peristaltic pumps, and valve arrangements releasing fluids from pressurized bottles and the like, without limitation.

While the invention has been described with reference to preferred embodiments, many modifications and variations will now occur to persons skilled in the art. For a definition of the invention, reference is made to the following claims.

We claim:

1. A method for controlling operation of an ozone generator in which ozone is generated by converting oxygen within an oxygen containing gas in a corona discharge mechanism by corona discharge of electromagnetic radiation through the oxygen containing gas by providing electrical power to the corona discharge mechanism to render the corona discharge mechanism operative to convert oxygen to ozone, and in which the amount of ozone generated with time is a function of one or more of the voltage, amperage and frequency of the electrical power provided to the corona discharge mechanism, the method comprising:
sensing with a sound sensor sound created by the corona discharge mechanism while operative to convert oxygen into ozone with time,
estimating an amount of ozone generated with time as a function of the sound sensed by the sound sensor and
controlling the amount of ozone generated with time by controlling one or more of the voltage, amperage and frequency of the electrical power provided to the corona discharge mechanism as a function of the estimate of the amount of ozone generated with time.

2. A method as claimed in claim 1 wherein the sound is an ultrasonic sound, an infrasonic, sound or an audible sound, and
the method includes one or more of:
sensing with the sound sensor a frequency of the sound, measuring with the sound sensor the sound at different wavelengths or ranges of wavelength, and measuring with the sound sensor an intensity of the sound.

3. A method as claimed in claim 2 wherein the corona discharge mechanism is an open spark type corona discharge generator in which electricity is passed through air as the oxygen containing gas between two electrodes at different electrical potentials.

4. A method as claimed in claim 3 including:
establishing the function for estimating the estimate of the amount of ozone generated with time from the sound sensed by the sound sensor by the steps of:
i. test operating the ozone generator to produce ozone under varying conditions of operation and during such test operating, measuring with time with an ozone sensor test ozone produced with time and measuring with the sound sensor test sound created with time by operation of the ozone generator corona discharge mechanism, and
ii. using the measured test ozone produced with time and the measured test sound created with time to provide the function for estimating the estimate of the amount of ozone generated with time as representing a relationship between the measured test ozone produced with time and the measured test sound created with time under the varying conditions of operation.

5. A method of operating a hand cleaner dispenser comprising:
generating ozone in an ozone generator in a chamber in which ozone is generated by converting oxygen in an oxygen containing gas to ozone to produce ozonated air containing ozone in a corona discharge mechanism by the corona discharge of electromagnetic radiation through the oxygen containing gas by providing electrical power to the corona discharge mechanism to render the corona discharge mechanism operative to convert oxygen to ozone, and in which the amount of ozone generated with time is a function of one or more of the voltage, amperage and frequency of the electrical power provided to the corona discharge mechanism,
passing the ozonated air and a liquid through a foam generator to generate a foamed mixture of the ozonated air and the liquid out a discharge outlet,
producing sound in the generation of the ozone,
sensing with a sound sensor sound created by operation of the corona discharge mechanism,
estimating an estimate of the amount of ozone generated with time as a function of the sound sensed by the sound sensor,
controlling the amount of ozone generated with time by controlling one or more of the voltage amperage and frequency of the electrical power provided to the corona discharge mechanism as a function of the estimate of the amount of ozone generated with time.

6. A method as claimed in claim 5 including delivering atmospheric air to the chamber to serve as the oxygen containing gas.

7. A method as claimed in claim 5 wherein the sound sensor is within the chamber.

8. A method as claimed in claim 5 wherein the sound sensor is outside to the chamber.

9. A method as claimed in claim 5 including controlling the operation of the ozone generator as a function of the estimate of the amount of ozone generated with time and the ozonated air passed through the foam generator.

10. A method as claimed in claim 9 including sensing at least one gas condition of the oxygen containing gas selected from the group of:
temperature, humidity and pressure, and estimating the amount of ozone generated with time as a function of the sound sensed by the sound sensor and the at least one gas condition.

11. A method as claimed in claim 5 wherein the sound is an ultrasonic sound, an infrasonic sound or an audible sound.

12. A method as claimed in claim 5 wherein a frequency of the sound is sensed by the sound sensor.

13. A method as claimed in claim 5 wherein the sound is measured at different wavelengths or wavelength ranges by the sound sensor.

14. A method as claimed in claim 5 wherein an intensity of the sound is sensed by the sound sensor.

15. A method as claimed in claim 5 including sensing the sound at a plurality of different locations.

16. A method as claimed in claim 5 wherein the method includes one or more of:
a. sensing with the sound sensor a frequency of the sound,
b. measuring with the sound sensor the sound at different wavelengths or ranges of wavelength, and
c. measuring with the sound sensor an intensity of the sound.

17. A method as claimed in claim 16 including:
establishing the function for estimating the estimate of the amount of ozone generated with time from the sound sensed by the sound sensor by the steps of:
i. test operating the ozone generator to produce ozone under varying conditions of operation and during such test operating, measuring with time with an ozone sensor test ozone produced with time and measuring with the sound sensor test sound created with time by operation of the ozone generator corona discharge mechanism, and ii. using the measured test ozone produced with time and the measured test sound created with time to provide the function for estimating the estimate of the amount of ozone generated with time as representing a relationship between the measured test ozone produced with time and the measured test sound created with time under the varying conditions of operation.

18. A method as claimed in claim 16 wherein the corona discharge mechanism is an open spark type corona discharge generator in which electricity is passed through air as the oxygen containing gas between two electrodes at different electrical potentials.

19. A method as claimed in claim 18 including:
establishing the function for estimating the estimate of the amount of ozone generated with time from the sound sensed by the sound sensor by the steps of:
i. test operating the ozone generator to produce ozone under varying conditions of operation and during such test operating, measuring with time with an ozone sensor test ozone produced with time and measuring with the sound sensor test sound created with time by operation of the ozone generator corona discharge mechanism, and
ii. using the measured test ozone produced with time and the measured test sound created with time to provide the function for estimating the estimate of the amount of ozone generated with time as representing a relationship between the measured test ozone produced with time and the measured test sound created with time under the varying conditions of operation.

20. A method as claimed in claim 5 wherein the corona discharge mechanism is an open spark type corona discharge generator in which electricity is passed through air as the oxygen containing gas between two electrodes at different electrical potentials.

* * * * *